United States Patent [19]
van den Hurk et al.

[11] Patent Number: 6,015,795
[45] Date of Patent: Jan. 18, 2000

[54] BOVINE VIRAL DIARRHEA VIRUS II VACCINE AND METHOD OF IMMUNIZATION

[75] Inventors: Jan van den Hurk, Saskatoon; Peter Tijssen, Pointe Claire, both of Canada

[73] Assignee: Biostar, Inc., Saskatoon, Canada

[21] Appl. No.: 09/008,722

[22] Filed: Jan. 19, 1998

Related U.S. Application Data

[60] Division of application No. 08/445,746, May 22, 1995, Pat. No. 5,709,865, which is a continuation-in-part of application No. 08/337,618, Nov. 10, 1994, abandoned.

[51] Int. Cl.[7] ............................. A61K 48/00; C07H 21/04
[52] U.S. Cl. ....................... 514/44; 424/218.1; 435/69.1; 435/172.1; 530/300; 530/350; 536/23.72
[58] Field of Search ........................... 424/218.1; 514/44; 435/69.1, 172.1; 530/300, 350; 536/23.72

[56] References Cited

U.S. PATENT DOCUMENTS 5,206,163  4/1993  Renard et al. .

OTHER PUBLICATIONS

Becher, P. et al., "Molecular Characterization of Border Disease Virus, a Pestivirus from Sheep," *Virology* 198:542–551 (1994).

Paton, D.J. et al., "Epitope Mapping of the gp53 Envelope Protein of Bovine Viral Diarrhea Virus," *Virology* 190:763–772 (1992).

Paton, D.J. et al., "Stability of the gp53 Gene of a Bovine Viral Diarrhoea Virus Isolated at Different Times from a Persistently Infected Steer," *Br. Vet. J. 150*:603–607 (1994).

Pellerin, C. et al., "Identification of a New Group of Bovine Viral Diarrhea Virus Strains Associated with Severe Outbreaks and High Mortalities," *Virology 203*:260–268 (1994).

Ridpath, J.F. et al., "Segregation of Bovine Viral Diarrhea Virus into Genotypes," *Virology 205*:66–74 (1994).

Sullivan, D.G. and Akkina, R., "Protein and Genomic Analysis of Border Disease Virus," Abstract, presented at IXth Int'l Congress of Virology, Glasgow, Scotland, Aug. 8–13 (1993).

Sullivan, D.G. et al., "Structural Gene Analysis of Border Disease Virus, " Abstract, presented at 74th Conf. of Research Workers in Animal Diseases, Fort Collins, Colorado, USA, Nov. 8–9 (1993).

Sullivan, D. G. et al., "Nucleotide Sequence Analysis of the Structural Gene Coding Region of the Pestivirus Border Disease Virus," *Virus Research 33*:219–228 (1994).

*Primary Examiner*—Mary E. Mosher
*Assistant Examiner*—Ali R. Salimi
*Attorney, Agent, or Firm*—Charles K. Sholtz; Dehlinger & Associates

[57] ABSTRACT

This invention relates to the identification of Bovine Viral Diarrhea Virus group II (BVDV-II) nucleic acid sequences (e.g., gp53 sequences), to methods of using the nucleic acid sequences for detecting BVD-II virus in animal sera, to polypeptide viral antigens derived from the sequences and immunoreactive with sera from animals infected with Bovine Viral Diarrhea group II (BVD-II) virus, to polynucleotide sequences which encode these polypeptide antigens, to an expression system capable of producing the polypeptide antigens, to vaccines containing the polypeptide antigens, to methods of using the polypeptide antigens for detecting BVD-II virus antibodies in animal sera, and to antibodies directed against these polypeptide antigens.

2 Claims, 12 Drawing Sheets

TTAACTAGGATTTGGAACGCTGCCACCACAACAGCCTTCCTAGTCTTCCTTGTGAAAGTACT
GAGGGGACAATTAATCCAAGGGCTATTGTGGCTGATGCTAATAACAGGGGCACAGGGCTTCC
CTGAATGCAAAGAGGGCTTCCAATATGCCATATCAAAAGACAAAAAAATAGGACCACTGGGG
CCAGAGAGTCTAACTACAACATGGCACCTTCCTACCAAAAAAATAGTGGACTCTATGGTACA
GGTGTGGTGTGATGGAAAAGACTTGAAAATATTAAAAACGTGCACAAAGGAAGAGAGGTACT
TAGTGGCCGTGCACGAAGAGCCCTGTCGACCAGTGCTGAGTTCATGCAGATCAGTAGTGGG
ACAAAAGGCCCAGAAGTGATAGATATGCCTGATGACTTTGAATTTGGACTCTGCCCTTGTGA
TTCAAAACCGGTAATAAAGGGGAAGTTCAATGCCAGCTTATTGAACGGACCAGCTTTCCAGA
TGGTATGCCCACAGGGGTGGACTGGTACAATAGAATACATCCTGGCGAACCAAGACACCTTG
GACACAACTGTCGTTAGGACATATAGAAGAACTACTCCATTTCAGCGGAGAAAATGGTGTAC
CTATGAAAAGATAATAGGGGAAGATATCCATGAATGCATTCTAGGAGGAAACTGGACATGCA
TAACTGGTGACCATAGCAAGTTGAAAGATGGGCCTATCAAGAAGTGTAAGTGGTGTGGCTAC
GACTTCTTCAATCCAGAAGGACTGCCACACTACCCAATAGGTAAGTGCATGCTCAGCAATGA
GAGTGGGTACAGGTTAGATGACACCTCTTGTGATAGGGGTGGTGTAGCCATAGTTCCAACAG
GTACCGTAAAGTGTAGAATAGGCAACACCACGGTGCAGGTTATCGCTACTAACACTGACCTG
GGACCCATGCCCTGCAGCCCAGCTGAGGTGATAGCAAGTGAAGGACCAGTGGAAAAGACGGC
ATGCACGTTTAACTATTCAGAGACACTACCTAATAAGTATTATGAGCCAAGGGACCGGTACT
TCCAACAATACATGTTAAAAGGGAAGTGGCAATATTGGTTTGACCTGGATTCTATAGACCAC
CACAAAGACTACTTTTCAGAGTTCATAGTTATAGCAGTGGTAGCCTTGCTAGGTGGTAAGTA
TGTACTGTGGCTCTTAGTAACATATATGATACTGTCTGAGCAGATGGCTATGGGTGCTGGAG
TAAGTACCGAAGAGATAGTCATGATGGTCTAACTGCTTATGTAGTATCTTC

Fig. 1

```
LTRIWNAATTTAFLVFLVKVLRGQLIQGLLWLMLITGAQGFPECKEGFQYAISKDKKIGPL
GPESLTTTWHLPTKKIVDSMVQVWCDGKDLKILKTCTKEERYLVAVHERALSTSAEFMQISSGTK
GPEVIDMPDDFEFGLCPCDSKPVIKGKFNASLLNGPAFQMVCPQGWTGTIEYILANQDTLDTTVV
RTYRRTTPFQRRKWCTYEKIIGEDIHECILGGNWTCITGDHSKLKDGPIKKCKWCGYDFFNPEGL
PHYPIGKCMLSNESGYRLDDTSCDRGGVAIVPTGTVKCRIGNTTVQVIATNTDLGPMPCSPAEVI
ASEGPVEKTACTFNYSETLPNKYYEPRDRYFQQYMLKGKWQYWFDLDSIDHHKDYFSEFIVIAVV
ALLGGKYVLWLLVTYMILSEQMAMGAGVSTEEIVMMVZLLMZYL
```

Fig. 2

```
O-2341  CTAACGCGCA TTTGGACCGC TGCTACGACT ACTGCATTCC TGGTATGTCT GGTGAAGGTG
N-2342  T....A.... ......A... ...A..A... .....T..TT .A.....C.. T..T...A.A
B-2364  T....TA.G. .A....A.C. ...C..C..C ..A..T.... .AA.C.TCT. A.....A.CA
S-1     T....TA.G. ......A... ...C..C..A ..A..C.... .A..C.TC.. T.....A..A

O-2401  GTGAGAGGCC AAGTGTTGCA AGGCATACTG TGGTTGATAC TCATAACAGG GGCACAAGGG
N-2402  ..C..G.... .GA..G.A.. G.....T... ...C.AC..T .G........ ..T.......
B-2424  C....G..A. ..C.AA.T.. ...GC..T.. ...C....G. .A........ A..G..G..C
S-61    C....G..A. ..T.AA.C.. ...GC..T.. ...C....G. .A........ ......G..C

|--->gp53
        |
O-2461  CTCCCAGTTT GCAAACCCGG CTTTTACTAC GCCATAGCCA AAAATAATGA GATCGGCCCT
N-2462  .A.TTG.A.. ......T.A  A..C.CG..T ........A. .GG.CG.AAG A..T..T.AA
B-2484  T....T.AA. .....GAG.. ...CC.A..T ......TC.. ..G.C.GAA. A..G..GTTA
S-121   T....T.AA. .....GAG.. ...CC.A..T ......TCA. ..G.C..AA. A..A..GTT.

O-2521  CTTGGGGCTA CGGGCCTCAC CACTCAGTGG TATGAATACT CGGATGGGAT GCGGCTGCAG
N-2522  ..G......G AA.....T.. ...CACT... A.G....... .ACC...A.. .AA....G.A
B-2544  T.G...C.AG A.A..T.A.. T..AACA... C.CCTTCCCA .C------.A AAAAA.AGT.
S-181   ..G...C.AG A.A.T.A..  T..AACA... C.CCTTCCTA .C------.A AAAAA.AGT.

O-2581  GACACGGGAG TTGTAGTGTG GTGTAAAGGT GGAGAGATCA AATATCTAAT TACATGTGAG
N-2582  .....AATG. .CA.T.CT.. ...CG...A. ..GA..T.A. TG..C..CCA A.G...CAC.
B-2598  ...T.CATG. .ACA...A.. ....G....G AA...CT.G. ..ATATT..A A..G..CACA
S-235   ...T.TATG. .ACAG..... ....G.T..A AA...CT.G. ..ATATT..A A..G..CACA

O-2641  AGGGAAGCCA GGTATCTGGC CATTCTACAC ACGAGAGCCC TGCCGACGTC TGTAGTATTT
N-2642  ..A...A... .A.....C.. A..CT.G..T ...A......T ........CAG ...G.....C
B-2658  .A.....AG. ....C..A.T GGC.G.G... GA........ .AT.A.CAG ..CT.AG...
S-295   .A.....AG. ....CT.A.T GGCCG.G... GAA....... .GT....CAG ..CT.AG..C

O-2701  GAAAAAATCA TAGATGGAAA AGAACAAGAG GACGTAGTGG AAATGGATGA TAACTTTGAA
N-2702  A......C..T .T.....GCG .A.G...... ..T.....C. .....A.C.. C.........
B-2718  ATGC.G.... GT.....GGC .AT.GGCCCA ..T..GA.A. .T...AC... .G........G
S-355   ATGC.G.... GTAG...G.C .A...GGCCCA ..A...GA.A. .T...CC... .G........

O-2761  CTCGGTCTTT GCCCGTGTGA TGCTAAACCC TTGGTAAGGG GAAAATTTAA TACAACACTT
N-2762  T.T.A..C. ....A..... ...C...... A.A.....A. .G..G..C.. ......G..G
B-2778  T.T.A..C. ....T..... CT.A.....A G..A...A.. .C........ .G.C.GCT.A
S-415   T.T.A..C. ....T..... TT.A.....G G.AA...A.. .G..G..C.. .G.C.GCT.A
```

Fig. 3A

```
O-2821  CTGAATGGGC  CAGCCTTCCA  GATGGTTTGC  CCTATAGGAT  GGACAGGAAC  TGTGAGTCTG
N-2822  .....C..A.  .G........  ......A...  ..C.......  ........G..  ...A..---C
B-2838  ........A.  ....T..T..  ......A...  ..ACAG..G.  ....T..T.G  AA.AGA---A
S-475   T....C..A.  ....T.....  ......A...  ..ACAG..G.  ....T..T..  AA.AGA---A

O-2881  TGTCACTGGT  CCAATAAGGA  TACGTTAGCC  ATGACCGTTG  TACGAACATA  CAAGAGGCAC
N-2879  ...ACG.CA.  T.....T...  C..C......  .CA..T..G.  ....G.....  T.GA...TCT
B-2895  ..CAC.CTAG  .G..CC.A..  C..C..G.A.  .CA..T..C.  .TA.G.....  T.GA...AACT
S-532   .ACAT.CT.G  .G..CC.A..  C..C..G.A.  .CA..T..C.  .TA.G.....  T.GA...AACT

O-2941  AGGCCTTTCC  CCTTTAGGCA  AGGCTGCATT  ACCCAGAAAG  TCATCGGGGG  AGACCTCTAC
N-2939  .AA..A....  .TCA......  ......T..C  .....A..GA  ATC.G....A  G..T...C.T
B-2955  .CT..A..T.  AGCGG..AA.  ..TTGT..CC  TATG.A...A  .G.TA....A  ...TA..C.T
S-592   .CT..A..T.  AGCGG..AA.  .T.G..T.CC  TATG.A..GA  .A.TA....A  ...TA..C.T

O-3001  GACTGTGCCT  TGGGAGGGAA  CTGGACTTGT  GTACCGGGGG  ACATACTACG  ATATGTAGAT
N-2999  A....CAT.C  .T.....A..  T.........  ..G..T..A.  ..CA.....T  ...CAA..GG
B-3015  ..A..CATT.  .A..T..A..  ......A..C  A..A.T..T.  .ACATAGCAA  G.TGAA....
S-652   ..A..CATTC  .A......A..  ......A..C  A..A.T..T.  ...CATAGCAA  G.TGAA....

O-3061  GGGCCTGTCG  AGTCTTGCAA  GTGGTGTGGT  TACAAGTTTC  ATAAAAGTGA  GGGTCTGCCA
N-3059  ..CT..A.T.  .A........  .........C  ..TC.A...A  .AG.G.....  ...A..A...
B-3075  ..A..A..A  ..AAG..T..  .........C  ..TG.C..CA  .C..CTCA..  ...A......
S-712   ......A..A  ..AAG..T..  .........C  ...G.C..CT  TC..TCCA..  A..A......

O-3121  CACTTCCCAA  TTGGCAAGTG  CAAGCTGAAG  AATGAAAGTG  GCTACAGACA  AGTAGATGAG
N-3119  ....A...C.  ..........  T..AT..G..  ..C..G.C..  .T.....G.T  ......CAGT
B-3135  ....A.....  .A..T.....  ..T...C.TC  .....G....  .G.....GGT  .TGT..C---
S-772   ....A.....  .A..T.....  ..T...C.GC  .....G....  .G.....GTT  ..AT..C---

O-3181  ACCTCTTGCA  ACAGAGACGG  TGTGGCTATA  GTACCAACTG  GTTCGGTGAA  ATGCAAGATA
N-3179  ..........  .T.....A..  ......C...  ......CAA.  .GA.AT.A..  G.........
B-3192  ...C.....G  .T..G.GT..  ...A..C...  ..T.....A.  .CA.C..A..  G..T.GA...
S-829   ........TG  .T..G.GT..  ...A..C...  ..T.....A.  ...A.C..A..  G..T.GA...
                                       __|__
                                       GCCATA  Insert in BD-78, not in 1494

O-3241  GGGGACACAG  TGGTGCAAGT  CATAGCAATG  GATGATAAGC  TAGGGCCTAT  GCCTTGCAGA
N-3239  ..AA.A...A  CT..A..G..  ......T...  ...ACC..A.  .C..A.....  ..........
B-3258  ..TA..GTCA  C......G..  T..C..T.CT  A.CA..G.T.  .G..A..C..  ...C......C
S-889   ..CA....CA  C......G..  T..C..T.CT  A.CAC.G.C.  .G..A..C..  ...C......C
```

Fig. 3B

```
O-3301  CCATATGAAA  TCATTCCCAG  TGAGGGGCCG  GTAGAAAAGA  CGGCATGTAC  CTTCAACTAC
N-3299  ..........  ....AT.A..  ..........T  ..........  .A..G.....  T.........
B-3318  ...GC....G  .G..AG.A..  ...A.....A  ..G.......  .T.....C..  A.........
S-949   ...GC...GG  .G..AG.A..  ...A..A..A  ..G.......  ........C.  G..T......

O-3361  ACAAAAACAT  TAAAGAACAA  GTATTATGAG  CCTAGGGATA  ATTATTTCCA  ACAATACATG
N-3359  ..T..G....  .....A..T..  .....T....  ..C..A..C.  GC..C..T..  G.........
B-3378  T....G...C  ..CCT..T..  ..........  ..........  CC  GG..C.C...  ..........
S-1009  T..G.G...C  ..CCT..T..  ..........  ..A.....  CC  GG...C.....  ..........

O-3421  TTAAAAGGGG  AGTACCAATA  TTGGTTTGAC  CTAGAGATCA  CTGACCACCA  CCGGGATTAC
N-3419  C.......A.  ....T.....  C.........  ..G...G.G.  ........T..  ..........
B-3438  ..........  ...GG.....  ..........  ..G..TTCTG  TA........  .AAA..C...
S-1069  .........A  ...GG.....  ..........  ..G..TTCT.  TA........  .AAA..C...

O-3481  TTCGCTGAGT  CCCTACTGGT  GATAGTGGTT  GCACTCCTGG  GCGGTAGGTA  CGTGCTCTGG
N-3479  ..........  ..A...T.A..  .G.G..A..A  ..C...T...  .T..C..A..  T..A..T...
B-3498  ...T.A....  T.A..A.CA.  AGC......C  ..CT.GT...  .T....A...  ...A..G...
S-1129  ..TT.A....  T.A...G.TA.  AGC......A  ..CT.G..A.  .T....A...  T..A..G...

gp53<---|--->gp54
                                                              |
O-3541  TTACTGGTTA  CATATATGAT  CCTATCAGAA  CAAATGACCT  CGGGACGTCC  AGTATGGGCA
N-3539  ..........  ....C...G.  .T........  ..G.A.G...  TA..GAT..A  GTATG.AT..
B-3558  C.CT..A.A.  ....C.CA..  A..G.T..G  ..G...G.TA  ----------  ----------
S-1189  C.CT.A..A.  .......A..  A..G..T..G  ..G...G.TA  T...TGC.GG  ....A.TA.C

O-3601  GGTGAAATAG  TGATGATGGG  CAACCTGCTA
N-3599  ..G...G.G.  ..........  ....T.....
B-      ----------  ----------  ----------
S-1249  .AA..G....  .C.......T  .T.A.....T
```

Fig. 3C

```
                                                    gp47<---|--->gp53
O-   1  LTRIWTAATT TAFLVCLVKV VRGQVLQGIL WLILITGAQG LPVCKPGFYY AIAKNNEIGP
N-   1  .....N.... ..........I ....MV.... ..L....V.. HLD...E.S. ....DER..Q
B-   1  .....NP... ....IF...A L...LI.GL. ..M....... F.E..E..Q. ...S.DRKM.L
S-   1  .....N.... ....F...V  L...LI.GL. ..M....... F.E..E..Q. ...S.DKK...
X-164  ...V.NS.S. ....I..... L....V..LV ..L.V..... QFA.REDYR. .L.RTK...A

O-  61  LGATGLTTQW YEYSDGMRLQ DTGVVVWCKG GEIKYLITCE REARYLAILH TRALPTSVVF
N-  61  ...E....T. K...P..K.E ...M.IA..ED .KLM..QR.T ..T....... ..........
B-  61  ..PES...T. HLPT--KKIV .SM.Q...E. KDL.I.K..T K.E...VAV. E...S..AE.
S-  61  ..PES...T. HLPT--KKIV .SM.Q...D. KDL.I.K..T K.E...VAV. E...S..AE.
X-224  ...ES...T. TD.RGNLE.D .GT.RAT.SR .FFRFRGHCM IGP....S.. L........T.

O-121  EKIIDGKEQE DVVEMDDNFE LGLCPCDAKP LVRGKFNTTL LNGPAFQMVC PIGWTGTVSL
N-121  K.LF..RK.. .....N.... F......... I......... .......... ..........-
B-119  MQ.S..AIGP ..ID.T.D.. F......S.. VIK....AS. .......... .Q....RIE-
S-119  MQ.SS.TKGP E.ID.P.D.. F......S.. VIK....AS. .......... .Q.....IE-
X-284  .L.PG.SAMT E-E..G.D.. F......SR. V.K..YN... I..S...LI. .Y..V.R.E-

O-181  CHWSNKDTLA MTVVRTYKRH RPFPFRQGCI TQKVIGGDLY DCALGGNWTC VPGDILRYVD
N-180  .TSF.M.... T......R.S K...H..... ...NL.E..H N.I....... ....Q.L.KG
B-178  .TLA.Q...D T......R.T T..QR.KVVT YE.M..E.IH N.I....... IT.EHSKLK.
S-178  YILA.Q...D T......R.T T..QR.KW.T YE.I..E.IH E.I....... IT..HSKLK.
X-343  .TTVS.S... TE..KI..KT K..QQ.V..D HTT.YKQ... H.QM...... MR.EVVK..G

O-241  GPVESCKWCG YKFHKSEGLP HFPIGKCKLK NESGYRQVDE TSCNRDGVAI VPTGSVKCKI
N-240  .SI....... .Q.KE..... .Y......E ..T...L..S .....E.... ..Q.TL....
B-238  ..IKK..... .D.NN..... .Y.....M.I ......VC.- .P.D.G.... ....T...R.
S-238  ..IKK..... .D.FNP.... .Y.....M.S ......LD.- ...D.G.... ....T...R.
X-403  ...KK.E... .C.K.R.... .Y...R.M.R ..T...S..D .P.D.G..V. SK..ELE.L.
                                                   |
                                    Insert only in BD-78   AI O-301  GDTVVQVIAM DDKLGPMPCR PYEIIPSEGP VEKTACTFNY TKTLKNKYYE PRDNYFQQYM
N-300  .K.T...... .T........ .....S.... .......... .......F. ...S......
B-297  .NVT.....T NND......S .A.V.A.... .......... S...P..... ...R.S....
S-297  .N.T.....T NTD......S .A.V.A.... .......... SE..P..... ...R......
X-463  .K.T.K.FSS .K.......CR.K.V.S.... .S.I...... S...E..... ...S......
                            |- extra a.a. in X818 gp53<---|--->p54
O-361  LKGEYQYWFD LEITDHHRDY FAESLLVIVV ALLGGRYVLW LLVTYMILSE QMTSGRPVWA
N-360  .......... ..V....... .......V.. .......... ......V... .KAL.IQYGS
B-357  ....W..... .DSV...K.. .S.FII.AVV .....K.... ...I..T.... ..A
S-357  ...KW..... .DSI...K.. .S.FIVIAVV .....K.... .......... .AM.AGVST
X-524  ...Q...... ..A....S.. ...FIMLA.. .......... .M.V....AD ....AINLGQ
```

BOVINE VIRAL DIARRHEA VIRUS II VACCINE AND METHOD OF IMMUNIZATION

This application is a divisional of U.S. patent application Ser. No. 08/445,746, filed May 22, 1995, now U.S. Pat. No. 5,709,865, which is a continuation-in-part of U.S. patent application Ser. No. 08/337,618, filed Nov. 10, 1994, now abandoned, both of which are herein incorporated by reference.

FIELD OF THE INVENTION

This invention relates to the identification of Bovine Viral Diarrhea Virus group II (BVDV-II), to the isolation of BVDV-II nucleic and amino acid sequences, and to diagnostic and therapeutic methods applicable to BVDV-II.

REFERENCES

Ausubel, F. M., et al., *CURRENT PROTOCOLS IN MOLECULAR BIOLOGY*, John Wiley and Sons, Inc., Media Pa.

Beames, et al., *Biotechniques* 11:378 (1991).

Becher, et al., *Virology* 198:542–551 (1994).

Bielefeldt-Ohmann, H., et al., *J. Gen. Virol.* 68:1971–1982 (1987).

Bolin, S. R., and Ridpath, J. F., *Am. J. Vet. Res.* 53:2157–2163 (1992).

Briand, J. -P., et al., *J. Immunol. Meth.* 156:255 (1992).

Brock, K. V., et al., *J. Virol. Methods* 38:39–46 (1992).

Brownlie, J., et al., *Vet. Rec.* 114:535–536 (1984).

Burnette, W. M., *Anal. Biochem.* 112:195 (1981).

Chomczynski, P., and Sacchi, N., *Anal. Biochem.* 162:156–159 (1987).

Collett, M. S., et al., *Virology* 165:191–199 (1988a).

Collett, M. S., et al., *Virology* 165:200–208 (1988b).

Collett, M. S., et al., *J. Gen. Virol.* 69:2637–2643 (1988c).

Corapi, W. V., et al., *J. Virol.* 62:2823–2827 (1988).

Corapi, W. V., et al., *J. Virol.* 63:3934–3943 (1989).

Corapi, et al., *J. Am. Vet. Med. Assoc.* 196:590–596 (1990).

Crea, R., U.S. Pat. No. 4,888,286, issued Dec. 19, 1989.

Dayhoff, M. O., *ATLAS OF PROTEIN SEQUENCE AND STRUCTURE*, suppl. 3, National Biomedical Research Foundation, Washington, D.C. (1978).

Deng, R., and Brock, K. V., *Virology* 191:867–879 (1992).

Deregt, D., et al., *Can. J. Vet. Res.* 54:343 (1990).

Donis, R. O., et al., *J. Gen. Virol.* 69:77 (1988).

Doolittle, R. F., *OF URFs AND ORFs*, University Science Books (1986).

Eaton, M. A. W., et al., U.S. Pat. No. 4,719,180, issued Jan. 12, 1988.

Fenner, F., *Intervirology* 6:1–12 (1975).

Francki, R. I. B., et al., *Arch. Virol.* 2(Suppl.):228–229 (1991).

Gillespie, J. H., et al., *Cornell Vet.* 50:73–79 (1960).

Goeddel, D. V., *Methods in Enzymology* 185 (1990).

Guthrie, C., and G. R. Fink, *Methods in Enzymology* 194 (1991).

Harlow, E., et al., *ANTIBODIES: A LABORATORY MANUAL*, Cold Spring Harbor Laboratory Press (1988).

Hopp, T. P., et al., *Proc. Natl. Acad. Sci. U.S.A.*, 78:3824 (1981).

Howard, C. J., et al., *Vet. Microbiol.* 13:361–369 (1987).

Kowalski, J., and Denhardt, D. T., *Mol. Cell. Biol.* 9:1946 (1989).

Kowalski, J., et al., *Vaccine* 11:1100 (1993).

Meyers, G., et al., *Virology* 171:555–567 (1989).

Moennig, V., and Plagemann, P. G. W., *Adv. Virus Res.* 41:53–98 (1992).

Moormann, R. J. M., et al., *Virology* 177:184–198 (1990).

Moss, B., et al., *CURRENT PROTOCOLS IN MOLECULAR BIOLOGY* (Section IV, Unit 16) (1991).

Mullis, K. B., U.S. Pat. No. 4,683,202, issued Jul. 28, 1987.

Mullis, K. B., et al., U.S. Pat. No. 4,683,195, issued Jul. 28, 1987.

Needleman, S. B., et al., *J. Theoret. Biol.* 43:351 (1974).

Radostits, O. M., and Littlejohns, I. R., *Can Vet. J.* 29:513–528 (1988).

Rebhun, W. C, et al., *J. Vet. Intern. Med.* 3:42–46 (1989).

Reilly, P. R., et al., *BACULOVIRUS EXPRESSION VECTORS: A LABORATORY MANUAL* (1992).

Renard, A., et al., European Patent Application No. 86870095.6, Publication No. 0208672 (1987).

Roeder, P. L., and Harkness, J. W., *Vet. Rec.* 119:143–147 (1986).

Sambrook, J., et al., *MOLECULAR CLONING: A LABORATORY MANUAL*, Second Edition, Cold Spring Harbor Laboratory (Cold Spring Harbor, N.Y.) (1989).

Sanger, F., et al., *Proc. Natl. Acad. Sci. U.S.A.* 74:5463–5467 (1977).

Schulz, G. E., et al., *PRINCIPLES OF PROTEIN STRUCTURE*, Springer-Verlag New York Inc. (1979).

Smith, D. B., et al., *Gene* 67:31 (1988).

Tam, J. P., *Proc. Natl. Acad. Sci. U.S.A.* 85:5409 (1988).

Taylor, W. R., et al., *J. Molec. Biol.* 208:1 (1989).

Thiel, H. -J., et al., *J. Virol.* 65:4705–4712 (1991).

Tikoo, S. K., et al., *J. Virol.* 67:726 (1993).

Ulmer, J. B., et al., *Science* 259:1745 (1993).

Yoshio, T., et al., U.S. Pat. No. 4,849,350, issued Jul. 18, 1989.

BACKGROUND OF THE INVENTION

Bovine viral diarrhea virus (BVDV) is a small enveloped positive-stranded RNA virus and is classified, along with hog cholera virus (HOCV) and sheep border disease virus (BDV), in the pestivirus genus. Pestiviruses were previously classified in the Togaviridae family (Fenner, 1975), but studies on their genomic organization (Collett, et al., 1988b, c) allowed their reclassification within the Flaviviridae family along with the flavivirus and hepatitis C virus (HCV) groups (Francki, et al., 1991). However, more recent studies on genomic organization, virion composition, and genomic RNA structure (Thiel, et al., 1991; Brock, et al., 1992) suggest, instead, a distinct family for pestiviruses.

BVDV is a worldwide, economically important pathogen of cattle and can be distinguished, based on cell culture analysis, into cytopathogenic (CP) and noncytopathogenic (NCP) biotypes (Gillespie, et al., 1960). The NCP biotype is more widespread although both biotypes can be found in cattle (Moennig and Plagemann, 1992). If a pregnant cow becomes infected with an NCP strain, she can give birth to a persistently infected (PI) and specifically immunotolerant calf that will spread virus during its lifetime (Roeder and Harkness, 1986). The PI individual can succumb to mucosal disease (MD) and both biotypes can then be isolated from the animal (Brownlie, et al., 1984). Since these biotypes are antigenically similar, it is probable that the NCP strain goes through mutations to give rise to a CP strain instead of a superinfection with the latter (Howard, et al., 1987; Corapi, et al., 1988). Other clinical manifestations can include abortion, teratogenesis, and respiratory problems (Radostits and Littlejohns, 1988). Apart from MD, cattle infected with BVDV generally develop a mild diarrhea followed by the appearance of neutralizing antibodies with a rapid recovery (Radostits and Littlejohns, 1988). In addition, severe thrombocytopenia, associated with herd epidemics, that may result in the death of the animal (Rebhun, et al., 1989; Corapi, et al., 1989, 1990) has been described and strains associated with this disease seem more virulent than the classical BVDVs (Bolin and Ridpath, 1992).

Several economically-devastating BVDV outbreaks among both veal calves and older animals were recently observed in Canada. In 1993, the mortality rate among veal calves in Quebec increased four times and was estimated at 31.5% for grain-fed calves and 17.1% for milk-fed calves (overall mortality was 32,000 out of 143,000 calves; Dr. G. Rivard, Ministère de l'Agriculture, des Pêcheries et de l'Alimentation du Québec (MAPAQ), Québec, Québec, Canada).

SUMMARY OF THE INVENTION

In one aspect, the invention includes a method of detecting a pestivirus or nucleic acid thereof in a nucleic acid-containing sample. The method includes combining the sample with a polynucleotide probe that specifically hybridizes with a polynucleotide fragment having a sequence encoding a Bovine Viral Diarrhea Virus Group II (BVDV-II) gp 53 protein, such as SEQ ID NO:1, and detecting the presence of pestivirus nucleic acid/probe complexes formed by hybridization of the probe to a complimentary target. The detection of such complexes indicates the presence of a pestivirus or nucleic acid thereof in the sample. In specific embodiments, the sample may include serum or fecal material obtained from an animal, such as a ruminant (e.g., cow or goat) or a pig, and the pestivirus may be a BVD-II or a BD virus. In one embodiment, the detecting may be accomplished by hybridization of a probe containing at least one reporter moiety. Reporter moieties may include those utilized in standard detection methods, such as labeling the probe by biotinylation or radioactive isotopes. Negative-sense oligonucleotide probes and oligonucleotide primers specific for BVDV-II gp53 polynucleotides are also defined by the present invention. Both the probes and primers can be derived from the above-described BVDV-II gp53 coding sequences. In another embodiment, the detecting includes amplifying the viral sequences using, for example, polymerase chain reaction.

In another aspect, the invention includes a bovine viral diarrhea virus group II (BVDV-II) polynucleotide in substantially isolated form. The polynucleotide may be a DNA molecule, such as a cDNA molecule, or an RNA molecule. In one embodiment, the polynucleotide encodes a BVDV-II gp53. In a related embodiment, the polynucleotide is a BVDV-II gp53 cDNA or cDNA complement. In another related embodiment, the polynucleotide contains the sequence represented as SEQ ID NO:1. In one embodiment, the polynucleotide includes the coding strand, in a related embodiment, the polynucleotide includes the complementary strand. In another embodiment, the polynucleotide includes fragments of the complete coding region. In other embodiments, the polynucleotide is a probe useful for prophylactic, therapeutic and diagnostic applications.

In a related aspect, the invention includes a substantially isolated polynucleotide containing the sequence represented as SEQ ID NO:1 or a portion thereof, where the portion includes at least about 40 consecutive nucleotides. The polynucleotide may be a DNA molecule, such as a cDNA molecule, or an RNA molecule. In one embodiment, the polynucleotide includes the presented sequence. In a related embodiment, the polynucleotide includes the sequence of the complementary strand. In another embodiment, the polynucleotide includes fragments of the presented sequence. In yet another embodiment, the polynucleotide is a probe useful for prophylactic, therapeutic and diagnostic applications. One diagnostic application is hybridizing to sequences encoding BVDV-II gp53.

Another aspect of the present invention includes a chimeric gene operatively coding for a BVDV-II gp53 polypeptide antigen. In one embodiment, the polypeptide antigen is encoded by the sequence represented by SEQ ID NO:2.

Also included in the present invention is a bovine viral diarrhea virus group II (BVDV-II) polypeptide in substantially isolated form. In one embodiment, the polypeptide encodes BVDV-II gp53. In a related embodiment, the polypeptide is an antigenic portion (epitope) of the gp53 polypeptide. In a related aspect, the invention includes a substantially isolated polypeptide having the sequence represented as SEQ ID NO:2. In one embodiment, the polypeptide is an antigenic portion (epitope) of the polypeptide having the sequence presented as SEQ ID NO:2. The invention further includes a recombinant polypeptide consisting of a sequence corresponding to BVDV-II gp53, BVDV-II gp53 cDNA or complements thereof; a recombinant polypeptide made of a BVDV-II gp53 epitope; and a fusion polypeptide comprised of a BVDV-II gp53 polypeptide.

In a related aspect, the invention includes a substantially isolated polypeptide containing the sequence represented as SEQ ID NO:2 or an antigenic portion thereof.

Both polyclonal and monoclonal antibodies directed against BVDV-II gp53 epitopes, or against epitopes encoded by a portion of the sequence presented as SEQ ID NO:2, are also useful as therapeutic agents, for diagnostic tests, for the isolation of the BVDV-II gp53 polypeptide, and for screening of antiviral agents.

Also included in the invention are a purified preparation of polyclonal antibodies directed against a BVDV-II gp53 epitope; and monoclonal antibodies directed against BVDV-II gp53 epitopes.

The invention also includes immunoassays, including an immunoassay for detecting BVDV-II and BDV, comprising the incubation of a sample which is suspected of including BVDV-II or BDV with a probe antibody directed against an antigen/epitope of BVDV-II gp53, to be detected under conditions allowing the formation of an antigen-antibody complex; and detecting the antigen-antibody complex which contains the probe antibody. An immunoassay for the detection of antibodies which are directed against a BVDV-II gp53 antigen comprising the incubation of a sample suspected of containing BVDV-II or BDV with a probe polypeptide including an epitope of BVDV-II gp53, under conditions that allow the formation of an antibody-antigen complex; and distinguishing the antibody-antigen complex which contains the probe antigen.

Yet another aspect of the present invention includes an expression system and a method of producing a BVDV-II gp53 polypeptide. The method includes introducing into a suitable host a recombinant expression system containing an open reading frame (ORF), where the ORF has a polynucleotide sequence which encodes a BVDV-II gp53 polypeptide, and wherein the ORF is linked operably to a control sequence which is compatible with a desired host. In this approach the vector is designed to express the ORF in the selected host. The host is then cultured under conditions resulting in the expression of the ORF sequence. A number of expression systems can be used in this regard including the lambda gt11 expression system in an *Escherichia coli* host. Other expression systems include expression vectors for use in yeast, bacterial, insect, and mammalian cells. The expressed gp53 protein may be isolated by a variety of known methods, depending on the expression system employed. As one example, a beta-gal-gp53 fusion protein may be isolated by standard affinity methods employing an anti-beta-gal antibody.

The invention also includes a vaccine for immunizing a ruminant or pig against an infection caused by a pestivirus. The vaccine includes a BVDV-II polypeptide antigen and a pharmacologically acceptable vaccine vehicle. In one embodiment, the polypeptide antigen is BVDV-II gp53. In a related embodiment, the polypeptide antigen includes an epitope encoded by the sequence represented by SEQ ID NO:2. In specific embodiments, the ruminant may be a cow or a goat. In another embodiment, the vaccine further includes a BVDV-I polypeptide antigen, such as BVDV-I gp53.

In a related aspect, the invention includes a vaccine for immunizing a ruminant or pig against an infection caused by a pestivirus. The vaccine includes a chimeric gene operatively coding for a BVDV-II polypeptide antigen and a pharmacologically acceptable vehicle. The gene is effective to express the polypeptide antigen in the ruminant or pig. In specific embodiments, the ruminant may be a cow or a goat, and the polypeptide antigen may be BVDV-II gp53, or may be encoded by the sequence represented by SEQ ID NO:2. In another embodiment, the vaccine further includes a chimeric gene operatively coding for a BVDV-I polypeptide antigen, such as BVDV-I gp53.

Also included in the present invention is a diagnostic kit for use in screening ruminant or pig serum, containing serum antibodies, for a pestivirus. The kit includes a BVDV-II gp53 polypeptide antigen and a means for detecting the binding of the antigen to serum antibodies specifically immunoreactive with BVDV-II gp53 polypeptide. In specific embodiments, the polypeptide antigen may include an epitope encoded by the sequence represented by SEQ ID NO:2, and the detection means may include a reporter-labeled detection antibody and a solid support to which the polypeptide is attached. The binding of the antigen to the serum antibodies can be detected by binding of the reporter-labeled detection antibody to the solid support. In other specific embodiments, the ruminant may be a cow or a goat.

Another aspect of the present invention includes a method of screening ruminant or pig serum, containing serum antibodies, for a pestivirus. The method includes reacting serum from a pestivirus-infected ruminant or pig with a BVDV-II gp53 polypeptide antigen and examining the antigen for the presence of bound serum antibodies specifically immunoreactive with BVDV-II gp53 polypeptide. In one embodiment, the polypeptide antigen includes an epitope encoded by the sequence represented by SEQ ID NO:2. In another embodiment, the polypeptide antigen is attached to a solid support, the reacting includes reacting the serum with the support and subsequently reacting the support with a reporter-labeled detection antibody directed against the serum antibodies, and the examining includes detecting the presence of the reporter-labeled detection antibody on the solid support.

Yet another aspect of the present invention includes a method of detecting a pestivirus in a sample. The method includes contacting the sample with a substantially purified anti-BVDV-II gp53 antibody and examining the antibody for the presence of bound antigen. In one embodiment, the contacting includes contacting the sample with an antibody immobilized on a solid substrate, and the examining includes reacting said solid substrate with a reporter-labeled anti-BVDV-II gp53 antibody. In another embodiment, the contacting includes contacting the sample with an antibody immobilized on a solid substrate, and the examining includes reacting the solid substrate with a reporter-labeled BVDV-II gp53 polypeptide antigen reactive with the antibody. In other specific embodiments, the sample may include serum or fecal material obtained from an animal, such as a ruminant (e.g., cow or goat) or a pig, and the pestivirus may be a BVD-II or a BD virus.

These and other objects and features of the invention will become more fully apparent when the following detailed description is read in conjunction with the accompanying drawings.

BRIEF DESCRIPTION OF THE FIGURES

FIG. 1 shows the sequence of a nucleotide fragment encoding gp53 from BVDV isolate 1494.

FIG. 2 shows the sequence of an amino acid fragment corresponding to gp53 from BVDV isolate 1494.

FIGS. 3A, 3B and 3C show an alignment of the nucleic acid sequences of the Osloss, NADL, BD-78, and 1494 strains of BVDV in the region corresponding to gp53.

FIG. 4 shows an alignment of the amino acid sequences of Osloss, NADL, BD-78, 1494, and X818 strains of BVDV in the region corresponding to gp53.

FIGS. 6A, 6B and 6C show a comparison of the 5' UTR sequences between primers BV7 (SEQ ID NO:6) and BV8 (SEQ ID NO:7) from the following strains: NADL, SD-1, Singer, Oregon, C3, C1, NY-1, Draper, Osloss, Q47, Q713, Q69, Q1808, 1854, 890, CD87, Q111, Q140, Q126, Q2101, Q4812, 1494, Bull and Waters. The strains were grouped according to their nucleotide sequence homology and compared to a "representative" strain from each group. The numbers correspond to the NADL sequence.

BRIEF DESCRIPTION OF THE SEQUENCES

Figure 5:
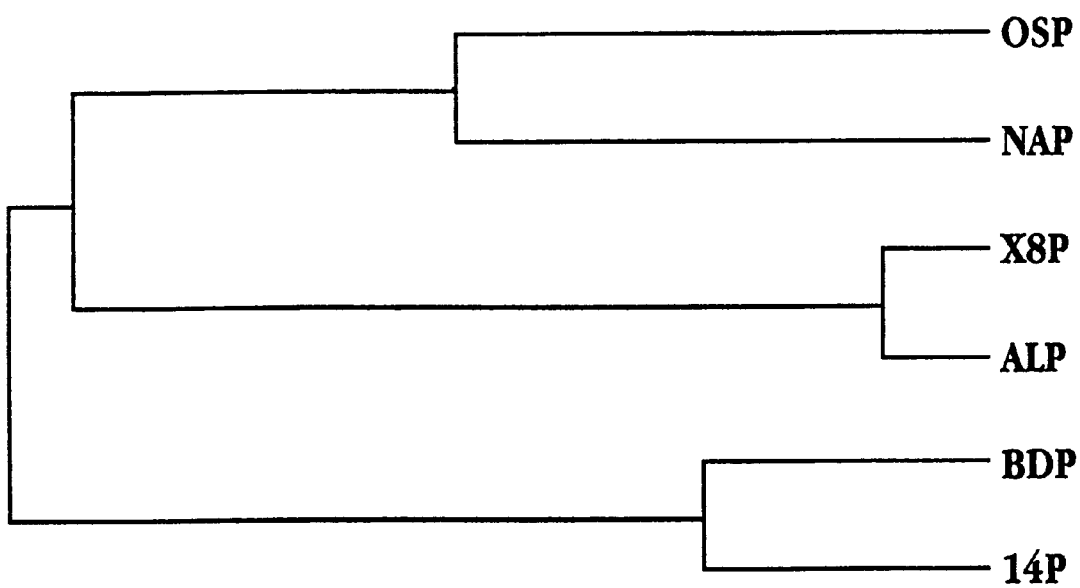
FIG. 5 shows a dendogram based on amino acid sequence alignments of BVDV sequences (containing gp53) from the following strains: Osloss, NADL, 1494, X818, BD-78, Alfort.

SEQ ID NO:1 is the polynucleotide sequence of a fragment containing the gp53 coding region from BVDV-II isolate 1494.

SEQ ID NO:2 is the predicted amino acid sequence from SEQ ID NO:1.

SEQ ID NO:3 is the polynucleotide sequence of primer $BV_{II}$ (3630 vicinity).

SEQ ID NO:4 is the polynucleotide sequence of primer pII-350 (3500 vicinity).

SEQ ID NO:5 is the polynucleotide sequence of primer pII-251 (2400 vicinity).

SEQ ID NO:6 is the polynucleotide sequence of primer BV7 (NADL nucleotides 392-372).

SEQ ID NO:7 is the polynucleotide sequence of primer BV8 (NADL nucleotides 103–123).

SEQ ID NO:8 is the polynucleotide sequence of BVDV Strain Singer 5' untranslated region (bases 1–248).

SEQ ID NO:9 is the polynucleotide sequence of BVDV Strain Waters 5' untranslated region (bases 1–248).

SEQ ID NO:10 is the polynucleotide sequence of primer 1A.

SEQ ID NO:11 is the polynucleotide sequence of primer 2A.

SEQ ID NO:12 is the polynucleotide sequence of primer 1B.

SEQ ID NO:13 is the polynucleotide sequence of primer 2B.

DETAILED DESCRIPTION OF THE INVENTION

I. Definitions

Bovine viral diarrhea group II (BVD-II) virus polynucleotides refer to polynucleotides derived from BVDV strains classified as group II, based on the guidance of the present specification (e.g., nucleic acid or sequence comparisons or serum virus neutralization titers). BVDV-II virus nucleotides also refer to variations of the disclosed sequences, such as degenerate codons, or variations in sequence which may be present in isolates or strains of BVD-II virus which are immunologically cross reactive with known BVDV-II strains, such as the 1494 isolate.

A protein is a BVD-II virus polypeptide or derived from a BVD-II virus polypeptide if it is encoded by an open reading frame of a cDNA or RNA fragment representing the BVD-II viral agent.

A protein having substantially the same sequence as one of the BVDV-II polypeptides is defined as a protein having amino-acid substitutions in the protein coding sequence which do not eliminate antigenic properties of the protein (i.e., neutral substitutions). Neutral substitutions not adversely affecting overall antigenic function are reasonably predictable by one of ordinary skill in the art by utilizing currently available primary and secondary structure analysis (Needleman, et al.; Doolittle; Taylor, et al., 1989; Hopp, et al.) coupled with a matrix defining the relatedness between different amino acids (Taylor, et al., 1989; Dayhoff; Schulz, et al). Proteins having sequence substitutions can be tested for immunoreactivity with sera, polyclonal, or specific monoclonal antibodies as described in the present disclosure.

An "epitope" is the area of an antigenic molecule (antigen) that determines the specific antibody to which the antigen binds.

An antigen or epitope is "specifically immunoreactive" with bovine viral diarrhea virus group II (BVDV-II) positive sera when the antigen or epitope binds to antibodies present in the BVDV-II infected sera with at least four-fold, and preferably at least six-fold, greater affinity than to antibodies in sera of animals that are not or have not been infected with BVDV-II or a closely-related virus, such as BDV. "Specifically immunoreactive" antigens or epitopes may also be immunoreactive with monoclonal or polyclonal antibodies generated against specific BVDV-II epitopes or antigens.

An antibody or antibody composition (e.g., polyclonal antibodies) is "specifically immunoreactive" with BVDV-II when the antibody or antibody composition is immunoreactive with a BVDV-II antigen but not with BVDV-I antigens. Further, "specifically immunoreactive antibodies" are not immunoreactive with antigens typically present in normal sera (i.e., sera not infected with or exposed to BVDV-II or a closely-related virus, such as BDV).

Two nucleic acid fragments are "homologous" if they contain at most about 20–30% basepair mismatches. More preferably, homologous nucleic acid strands contain 10–20% basepair mismatches. Two nucleic acid fragments are "highly homologous" if they have less than about 10% basepair mismatches (i.e., greater than about 90% nucleic acid sequence identity).

The term "specific hybridization", in the context of nucleic acid hybridization, is defined as hybridization under stringent conditions (Sambrook, et al.) of two nucleic acid fragments having greater than about 75% nucleic acid sequence identity. Fragments having less than about 75% nucleic acid sequence identity preferably do not "specifically hybridize" with one another under stringent hybridization conditions. Conditions favoring specific hybridization of highly homologous fragments depend on several factors, including the lengths of the fragments and the percent GC content of the fragments, and may be readily ascertained by one of skill in the art.

The term "gp53", when used in reference to a protein, refers to a viral protein that is homologous in either structure and/or function to glycoprotein 53 of BVDV virus. BVDV-II gp53 is a viral envelope glycoprotein that may encode a viral epitope.

A "ruminant" is an even-toed hoofed mammal of the suborder Ruminantia, comprising cloven-hoofed, cud-chewing quadrupeds (e.g., cattle, goats, buffalo, deer, llama, etc.).

II. Overview of the Invention

Experiments performed in support of the present invention describe the identification of a distinct group of BVDV isolates, based on both serology and sequence analysis (gp53, 5'UTR). This group, termed group II, comprises highly pathogenic strains of BVDV responsible for several recent deadly epidemics of BVD. Group II BVD virus strains are also closely related to the thrombocytopenic strains of BVDV, based on both sequence and serological data.

Also described is the isolation of a polynucleotide encoding a novel gp53 polypeptide derived from an isolate of BVD-II virus termed isolate 1494. The polynucleotides and corresponding polypeptides disclosed herein, as well as compositions and methods using these polynucleotides and polypeptides (as summarized above) have a number of uses in veterinary applications, such as the prophylactic, therapeutic and diagnostic applications outlined in the "Summary of the Invention", above.

III. Grouping of Pestiviruses

The pestivirus genus is a member of the flaviviridae family (Francki, et al., 1991) and includes bovine viral diarrhea virus (BVDV) of cattle, border disease virus (BDV) of sheep and hog cholera virus (HOCV) of pigs. The bovine viral diarrhea virus (BVDV) has until now been classified as a single viral species (Moennig and Plagemann). Results of experiments performed in support of the present invention, however, indicate that different strains of BVD viruses can be classified into at least two distinct groups, based on both serological and nucleotide sequence data, as described below.

A. Serological Data

Data shown in Example 1 (Table 2) illustrate the BVD viral neutralization (VN) activity of sera raised by infecting animals with various strains of BVDV. The ability of each serum to neutralize the infectivity of a panel of different BVDV strains (Draper, NADL, NY-1, Oregon, Singer, CD87, Waters, 890 and 1494 isolates) is tested. Based on the results of these and other studies, described below, the BVDV strains are classified into two serologically-distinct groups (BVDV group I and BVDV group II). The sera from animals infected with a strain belonging to one group (e.g., group I) are at least four times more effective at neutralizing viral infectivity of BVDV strains from that group than strains from the heterologous group (i.e., group II).

The validity of the classification of different BVDV isolates into groups I and II is further confirmed by virus neutralization studies using a set of anti-gp53 sera raised in rabbits and calves, shown in Examples 2 and 3, respectively.

Results shown in Example 2 (Table 3) are from experiments using sera from rabbits inoculated with affinity-purified group I (NADL strain) gp53. Results using both full length gp53 (FLgp53), as well as truncated gp53 (Tgp53) are presented. The sera are scored for their virus neutralization titers against several BVDV Group I and Group II isolates, essentially as in Example 1. The data show that gp53 as well as Tgp53 from a group I BVDV strain (NADL) are effective at neutralizing viral infectivity of other group I isolates, but are at least 9-fold less effective at neutralizing infectivity of group II BVDV isolates. These results suggest that the gp53 protein of group I strains is different enough from the gp53 protein of group II strains that the majority of neutralizing antibodies raised against one of the proteins do not cross-react with the other.

Accordingly, an immunological preparation, such as a vaccine, employing group I proteins (e.g., group I gp53), would not be expected to result in the effective production of antibodies in the inoculated animal specifically immunoreactive with group II proteins (e.g., group II gp53). By extension, such a vaccine would not be expected to be very effective against group II BVDV isolates.

Similarly, as illustrated in Example 3 and Table 4, sera from calves (negative for BVDV antibody and virus) immunized with either affinity purified FLgp53 or Tgp53 derived from the NADL strain (group I BVDV) neutralize group I BVDV over ten times more effectively than group II BVDV.

Taken together, the above results indicate that the BVDV family of viruses is comprised of at least two groups of viruses; group I BVDV and group II BVDV. The results suggest that the optimal viral neutralization activity against a particular target strain is afforded by neutralizing antibodies from sera of animals infected with a strain from the same group as the target strain. The results further suggest that an immunological preparation (e.g., a vaccine) effective against viral strains from one group (e.g., BVDV-II), preferably contains antigens (e.g., gp53) derived from viruses belonging to that group (BVDV-II), rather than the heterologous group (e.g., BVDV-I).

In many cases, it may be desirable to provide a vaccine or immunological preparation effective against both group I and group II BVDV isolates. In this regard, the present invention contemplates a vaccine or immunological preparation which contains, or results in the production of, both BVDV-I and BVDV-II antigens (e.g., both group I gp53 and group II gp53).

IV. Polynucleotide and Amino Acid Sequence Analysis

A. Molecular Cloning of BVDV-II gp53

A polynucleotide fragment containing a region encoding a BVDV-II glycoprotein 53 (gp53) was isolated from the 1494 strain and sequenced as described in Example 4. The nucleic acid sequence is presented herein as SEQ ID NO:1 and shown in FIG. 1. The predicted amino acid sequence translated from SEQ ID NO:1, which includes the sequence of the gp53 protein, is presented herein as SEQ ID NO:2 and shown in FIG. 2.

An alignment of nucleic acid sequences from the Osloss, NADL, BD-78, and 1494 strains of BVDV in the region corresponding to gp53 is shown in FIG. 3. A similar alignment of the corresponding amino acid sequences is shown in FIG. 4. The initial (5') portion of the presented sequences corresponds to the end of gp47, the main portion corresponds to gp53, and the last (3') portion corresponds to the beginning of p54. The sequences are aligned in both FIGS. 3 and 4 as follows. Line 1 corresponds to the gp53 sequence of the Osloss isolate (O), line 2 to the NADL isolate (N), line 3 to the BD-78 (B) isolate, line 4 to the 1494 Saskatoon Isolate cloned and sequenced as described above, and line 5 (FIG. 4) to the X818 (X) isolate of border virus. A comparison of the 1494 nucleotide sequence with the sequences of related viruses reveals that regions as short as 39 consecutive nucleotides contain at least one basepair mismatch between the 1494 sequence and the next most homologous sequence.

The sequences were also analyzed on an IBM-compatible PC computer using the "CLUSTAL" program from the PC/GENE (IntelliGenetics, Inc., Mountain View, Calif.)) software package. "CLUSTAL" analyzes groups of sequences for their similarity to one another and presents the results in the form of a dendogram. The lengths of the arms of the dendogram reflect the degree of similarity among the sequences—shorter arms separating two sequences indicate that the sequences are similar, while longer arms indicate that they are more divergent.

The results of a "CLUSTAL" analysis of gp53 amino acid sequences from BVDV group I isolates Osloss (OSP) and NADL (NAP), BVDV group II isolate 1494 (14P), border disease virus (BDV) isolates X818 (X8P) and BD-78, and hog cholera virus (HOCV) isolate Alfort (ALP), as well as the sequence alignments presented in FIGS. 3 and 4, indicate that (i) strain 1494 and other BVDV-II strains are closely related to the BD-78 border disease virus (~90% amino acid sequence homology, ~87% nucleotide sequence homology), but not to other border disease viruses, such as X818;

(ii) strain 1494 is different from group I BVDV strains, such as Osloss and NADL (60–65% amino acid sequence homology, 65% nucleotide sequence homology); and (iii) Alfort hog cholera virus is closely related to X818 border disease virus (97% amino acid sequence homology), and both are intermediate in sequence homology to group I BVDVs (55–60% amino acid sequence homology) and to group II BVDVs (~55% amino acid sequence homology).

Although BVDV-II and BD-78 have a ~87% nucleic acid homology, BD-78 was heretofore associated only with border disease in sheep, and BVDV was heretofore associated only with viral diarrhea in cows. Results of experiments performed in support of the present invention suggest that some pathogenic forms of diarrhea disease in ruminants and pigs may be caused by a previously unrecognized group of highly-related viruses, including BVDV-II and BD-78. Accordingly, diagnostic, prophylactic and therapeutic methods disclosed herein as relating to BVDV-II in cows may be applicable to other unrecognized related viruses which may cause similar forms of diarrhea disease in other ruminants and in pigs.

B. Molecular Cloning of BVDV-II 5'UTR

Polynucleotide fragments containing a region encoding BVDV-II 5' untranslated region (5'UTR) are isolated using a number of BVDV isolates, including Singer, Oregon, C3, C1, NY-1, Draper, Q47, Q713, Q69, Q1808, 1854, 890, CD87, Q111, Q140, Q126, Q2101, Q4812, 1494, Bull and Waters. The sequence for the 5' untranslated region (5'UTR) of BVDV-I isolate Singer is given as SEQ ID NO:8. The sequence for the 5'UTR of BVDV-II isolate Waters is given as SEQ ID NO:9.

Figure 6A:
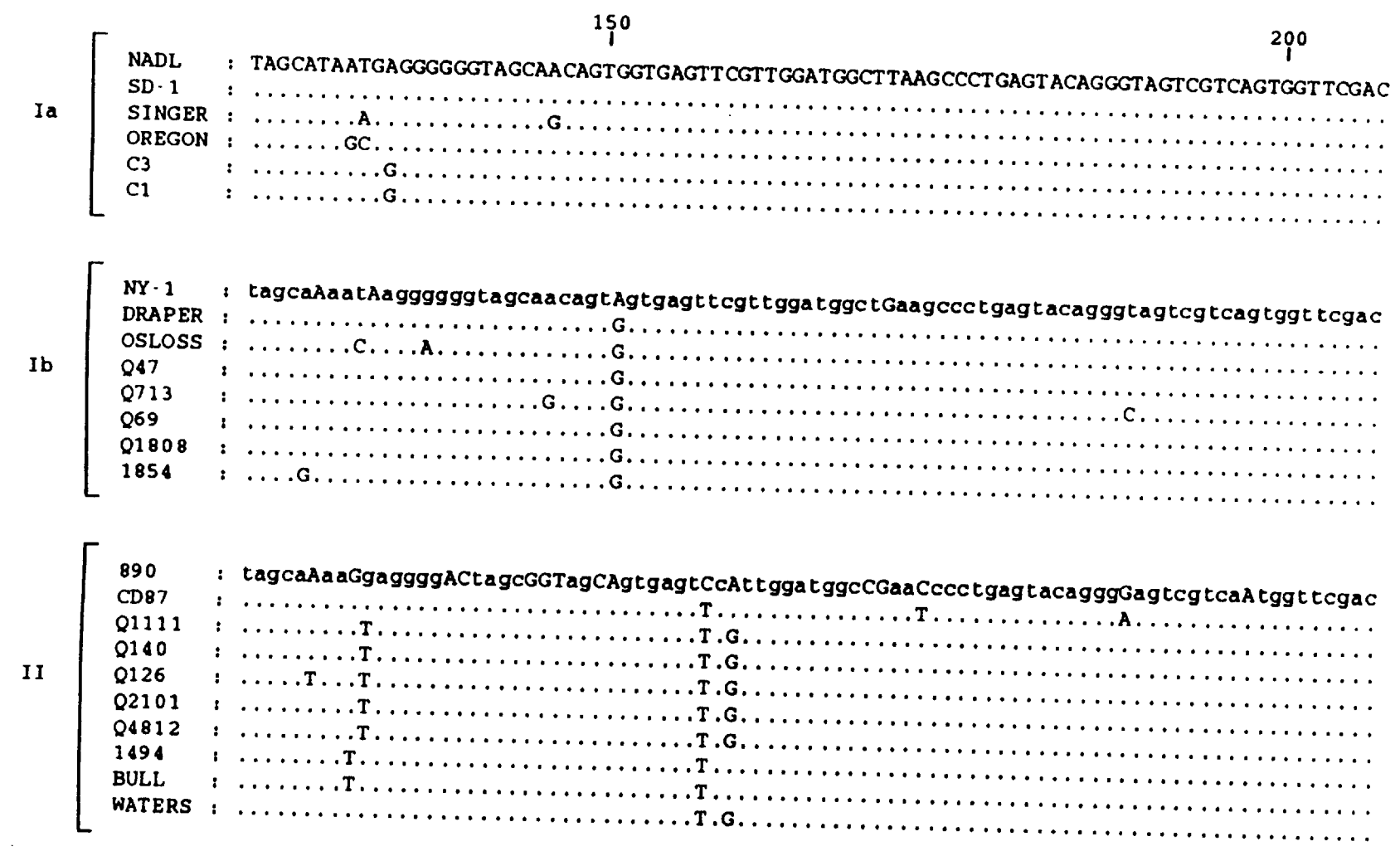
Figure 6B:
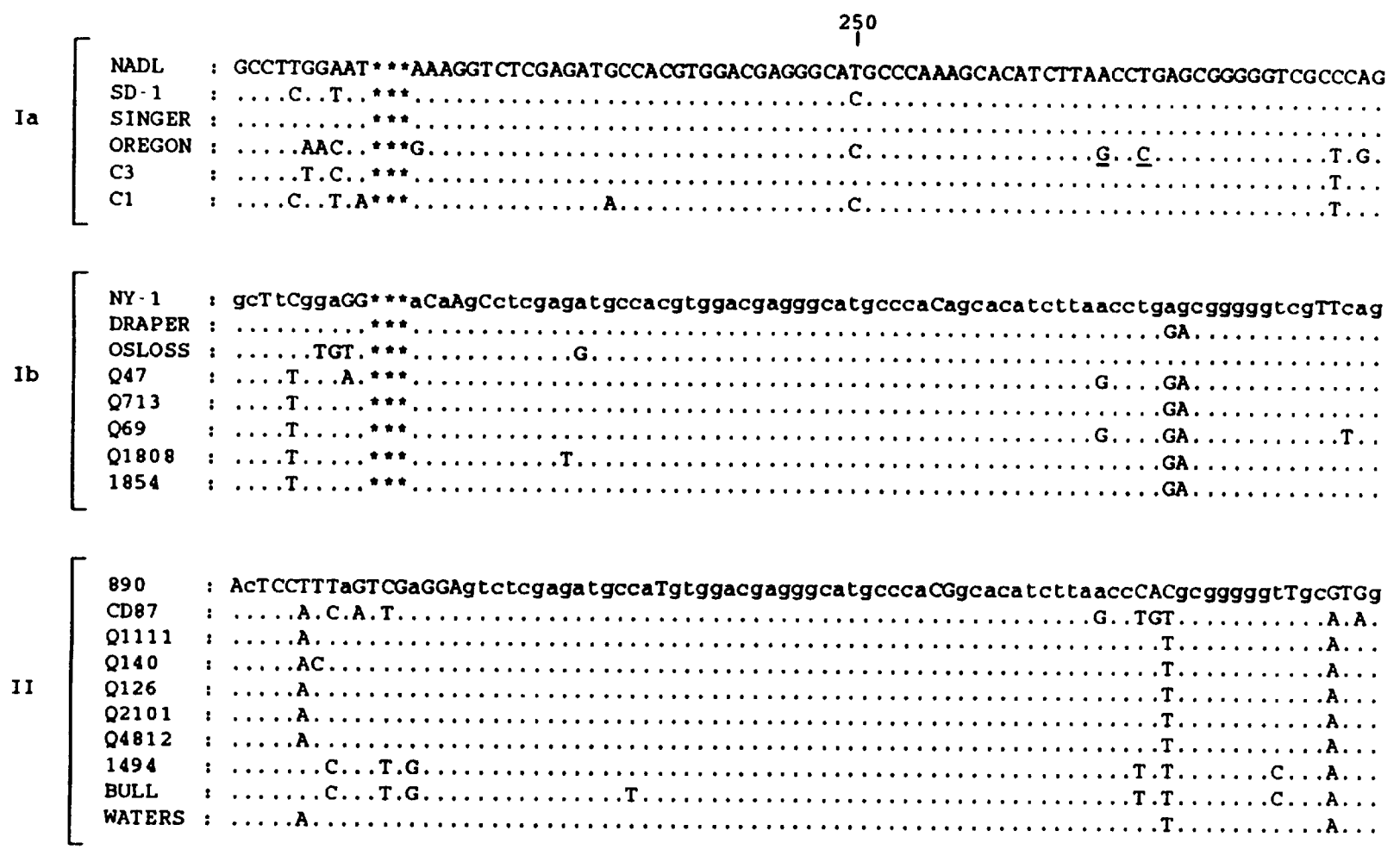
Figure 6C:
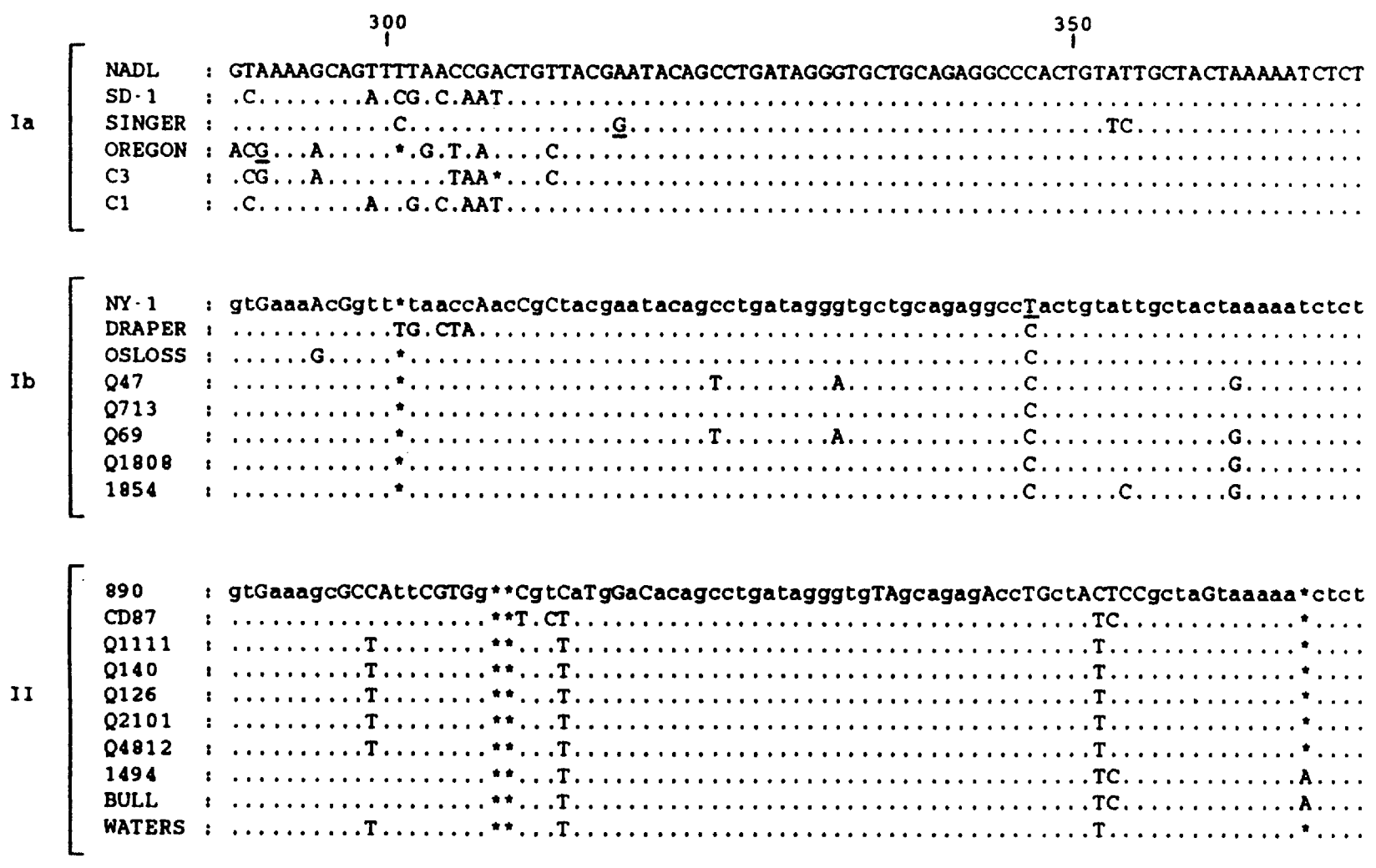

A comparison of the 21 5'UTR polynucleotide sequences, along with those of NADL, SD-1 and Osloss, are shown in FIG. 6. The data demonstrate that there exists a relatively high degree of homology among the 5'UTR sequences of all the pestiviruses, and an even higher degree of homology among isolates belonging to either group I or group II. Note that this analysis also illustrates a sub-grouping among the group I isolates (indicated in FIG. 6 as group Ia and group Ib).

C. Isolation of Genomic BVDV-II Sequences

Additional BVDV-II viral sequences may be isolated following the guidance presented herein and methods known to those skilled in the art. For example, viral agents suitable for the isolation of viral RNA may be obtained from a variety of sources, including blood, serum, saliva and fecal material from infected animals, as well as cell culture medium from infected tissue culture cells. The RNA may be purified using, for example, methods detailed in Example 4A, such as the guanidinium isothiocyanate method described by Chomczynski and Sacchi (1987).

The purified RNA may be used to generate cDNA libraries, which can be screened for desired sequences using probes from related viruses. The libraries may be constructed in any suitable vector (e.g., lambda gt11 or gt10). According to one known method of library construction, infected serum is precipitated with 8% polyethylene glycol (PEG), and the libraries are generated from RNA isolated from the resulting precipitated virus. Ultracentrifugation may also be used to pellet particulate agents from infected sera or other biological specimens.

cDNA libraries may be generated using known protocols (e.g., Sambrook, et al.,; Ausubel, et al.). Typically, random primers (e.g., hexamers) are employed in reverse transcription reactions using RNA extracted from pelleted sera (as described above). The cDNA molecules so produced may be cloned into a suitable vector (e.g., lambda gt11) for expression and screening of peptide antigens.

Lambda gt11 is a particularly useful expression vector. It contains a unique EcoRI insertion site 53 base pairs upstream of the translation termination codon of the β-galactosidase gene. An sequence inserted into this site is therefore expressed as a β-galactosidase fusion protein which contains the N-terminal portion of the β-galactosidase gene product, the heterologous peptide, and optionally the C-terminal region of the β-galactosidase peptide. It will be appreciated that the C-terminal portion is expressed only if the heterologous peptide coding sequence does not contain a translation termination codon.

Alternatively, viral RNA may be used as a template for polymerase chain reaction (PCR) to isolate novel BVDV-II sequences. An exemplary application of PCR for the isolation of BVDV-II viral sequences is presented in Examples 4 and 5, below. The RNA is typically reverse transcribed to generate first-strand cDNA polynucleotides, and the reaction products from the reverse transcription reaction are used as a template for a PCR reaction. The primers employed in the PCR reaction may be selected based on conserved regions of the viral genome of related pestiviruses.

Amplification products from a PCR reaction may be cloned using, for example, a "T/A" overhang cloning scheme (as described in Example 4E). Amplification products may also be cloned using blunt-end cloning, or by incorporating restriction sites at the 5' ends of the primers and digesting the amplified fragments. A variety of vectors may be employed, such as the "pCRII" T/A vector (Invitrogen, San Diego, Calif.), "BLUESCRIPT" vectors (Stratagene, La Jolla, Calif.), "pGEM" vectors (Promega Corp., Madison, Wis.) and the like.

BVDV-II DNA fragments (e.g., gp53; SEQ ID NO:1) may be isolated by polymerase chain reaction or by restriction endonuclease digestion of vectors carrying such sequences. The fragments can then be employed as labeled (e.g., radiolabeled) probes in hybridization experiments to screen a selected DNA or cDNA library to identify overlapping BVDV-II sequences, which can in turn be used as probes to identify additional, contiguous, clones. The 5' and 3' terminal sequences of the clone inserts are particularly useful as probes to identify additional overlapping clones. Using such an approach, it is possible to elucidate the sequence of the entire BVDV-II genome.

Promising clones may be sequenced using standard methods (e.g., the dideoxy method of Sanger, et al., 1977) and/or kits (e.g., the AutoRead sequencing kit, available from Pharmacia Biotech, Piscataway, N.J.). Reading of sequences may be facilitated with an automated system, such as the Automated Laser Fluorescent (ALF) DNA sequencer (Pharmacia Biotech).

V. Isolated Viral Polypeptides

Polynucleotide sequences of the present invention may be cloned into an expression plasmid, such as p-GEX, to produce corresponding polypeptides. The plasmid pGEX (Smith, et al., 1988) and its derivatives express the polypeptide sequences of a cloned insert fused in-frame with glutathione-S-transferase.

Recombinant pGEX plasmids can be transformed into appropriate strains of E. coli and fusion protein production can be induced by the addition of IPTG (isopropyl-thio galactopyranoside). Solubilized recombinant fusion protein can then be purified from cell lysates of the induced cultures using glutathione agarose affinity chromatography. Affinity chromatography is also employed for isolating β-galactosidase fusion proteins (such as those produced by lambda gt11 clones). The fused protein is isolated by passing cell lysis material over a solid support having surface-bound anti-β-galactosidase antibody.

Insoluble fusion protein may be purified using combinations of centrifugation to remove soluble proteins followed by solubilization of insoluble proteins. The solubilized proteins can then be processed using standard chromatographic methodologies, such as ion exchange or size exclusion chromatography, and other such methods are known in the art.

Isolated (e.g., recombinant) viral polypeptides of the present invention can be purified by standard protein purification procedures which may include differential precipitation, molecular sieve chromatography, ion-exchange chromatography, isoelectric focusing, gel electrophoresis and affinity chromatography.

VI. Chimeric Genes

Also included in the invention is a chimeric gene, such as an expression vector, containing BVDV-II coding sequences and expression control elements which allow expression of the coding regions in a suitable host. The control elements generally include a promoter, translation initiation codon, and translation and transcription termination sequences, and an insertion site for introducing the insert into the vector.

The DNA encoding a desired polypeptide can be cloned into any number of commercially available vectors to generate expression of the polypeptide in the appropriate host system. These systems include the following: baculovirus expression (Reilly, et al.; Beames, et al.; Pharmingen; Clontech, Palo Alto, Calif.), vaccinia expression (Moss, et al.), expression in bacteria (Ausubel, et al.; Clontech), expression in yeast (Goeddel; Guthrie and Fink), and expression in mammalian cells (Clontech; Gibco-BRL, Ground Island, N.Y.). The recombinant polypeptides can be expressed directly or as fusion proteins. It will be appreciated that a number of additional, useful features may be engineered into the expression vectors. For example, leader sequences, which promote the secretion of the expressed sequences into culture medium, may be included.

The recombinantly produced BVDV-II polypeptides are typically isolated from lysed cells or culture media. Purification can be carried out by methods known in the art including salt fractionation, ion exchange chromatography, and affinity chromatography. Immunoaffinity chromatography can be employed using antibodies generated based on BVDV-II antigens identified by the methods of the present invention.

VII. Antigens

Antigen encoding DNA fragments can be identified by (i) immunoscreening, as described herein, or (ii) computer analysis of coding sequences (e.g., SEQ ID NO:1) using an algorithm (such as, "ANTIGEN," Intelligenetics, Mountain View, Calif.) to identify potential antigenic regions. An antigen-encoding DNA fragment can be subcloned, and the subcloned insert can then be fragmented by partial DNase I digestion to generate random fragments. Alternatively, the DNA may be cut at selected sites by specific restriction endonuclease digestion. The resulting DNA fragments can be inserted into a suitable vector (e.g., lambda gt11) and subjected to immunoscreening in order to provide an epitope map of the cloned insert.

Fragments of DNA encoding antigenic regions may be expressed recombinantly either as fusion proteins or isolated polypeptides. Since antigenic regions of polypeptides are generally relatively small, typically 6 to 10 amino acids in length (though smaller fragments have been identified as antigenic, for example, conformational epitopes), the amino acid sequences can be conveniently chemically synthesized using commercially available polypeptide synthesizers (e.g., Applied Biosystems, Foster City, Calif.) or "PIN" technology (Applied Biosystems).

The present invention also contemplates mosaic proteins that are composed of multiple epitopes. A mosaic polypeptide typically comprises at least two epitopes of BVDV-II which, in the native BVDV-II coding sequence, may be separated by intervening sequences. Synthetic genes (crea; Yoshio, et al.; Eaton, et al.) encoding multiple, tandem epitopes can be constructed that will produce mosaic proteins using standard recombinant DNA technology and one of the polypeptide expression vector/host systems described above.

Further, multiple antigen peptides can be synthesized chemically by methods described previously (Tam, 1988; Briand, et al.). For example, a small immunologically inert core matrix of lysine residues with α- and e- amino groups can be used to anchor multiple copies of the same or different synthetic peptides (typically 6–15 residues long) representing epitopes of interest. Mosaic proteins or multiple antigen peptide antigens give higher sensitivity and specificity in immunoassays due to the signal amplification resulting from distribution of multiple epitopes.

Antigens obtained by any of these methods can be used for antibody generation, diagnostic tests and vaccine development.

VIII. Vaccines and Other Immunological Preparations

Vaccines or immunological preparations useful for immunizing an animal, such a ruminant (e.g., cow or goat) or a pig against BVDV-II can be prepared from one or more of the immunogenic polypeptides (e.g., gp53) identified by the method of the present invention. Genomic organization similarities between the isolated sequences from BVDV-II and other known viral proteins may provide information concerning the polypeptides that are likely to be candidates for effective vaccines. In addition, a number of computer programs can be used for to identify likely regions of isolated sequences that encode protein antigenic determinant regions (for example, Hopp, et al.; "ANTIGEN," Intelligenetics, Mountain View Calif.).

Vaccines containing immunogenic polypeptides as active ingredients are typically prepared as injectables either as solutions or suspensions in a pharmacologically acceptable vehicle. Further, the immunogenic polypeptides may be prepared in a solid or lyophilized state that is suitable for resuspension, prior to injection, in an aqueous form. The immunogenic polypeptides may also be emulsified or encapsulated in liposomes. The polypeptides are frequently mixed with pharmaceutically acceptable excipients compatible with the polypeptides, including the following and combinations of the following: saline, water, sugars (such as dextrose and sorbitol), glycerol, alcohols (such as ethanol [EtOH]), and others known in the art. Further, vaccine preparations may contain minor amounts of other auxiliary substances such as wetting agents, emulsifying agents (e.g., detergents), and pH buffering agents. In addition, a number of adjuvants are available which may enhance the effectiveness of vaccine preparations. Examples of such adjuvants include, but are not limited to, the following: VSA3 adjuvant (Biostar, Saskatoon, SK, Canada), the group of related compounds including N-acetyl-muranyl-L-threonyl-D-isoglutamine and N-acetyl-nor-muranyl-L-alanyl-D-isoglutamine, and aluminum hydroxide.

The immunogenic polypeptides used in the vaccines and immunological preparations of the present invention may be recombinant, synthetic or isolated from, for example, attenuated BVDV-II viruses. The polypeptides are commonly formulated into vaccines in neutral or salt forms. Pharmaceutically acceptable organic and inorganic salts are well known in the art. BVDV-II vaccines and immunological preparations are parenterally administered, typically by subcutaneous or intramuscular injection.

Vaccines may also be formulated using an expression vector encoding a viral antigen. Such "naked DNA" vaccine formulations have been shown to be effective, for example, in protecting mice against influenza infection (Ulmer, et al.). Expression vectors used in DNA vaccines contain the gene encoding the desired viral antigen under the control of a promoter effective to express the gene in the injected tissue. Non-replicating plasmids are advantageous as expression vectors in DNA vaccines because (i) an immune response against the vector itself is minimized, (ii) no infectious agent is involved, (iii) there is no assembly of virus particles, and (iv) determinant selection to optimize response for an individual animal's MHC haplotype is permitted.

An exemplary DNA vaccine against BVDV-II may be made by cloning a fragment containing the coding region for BVDV-II gp53 into an expression vector containing, for example, a Rous sarcoma virus (RSV) or cytomegalovirus (CMV) promoter. The resulting gp53 expression vector suspended in saline may be injected (e.g., intramuscularly) at selected intervals (e.g., once per week) over a selected time span (e.g., one month) to provide the desired level of protection. Protection may be measured by assaying for the presence of anti-gp53 antibodies in the treated animal's serum using, for example, one of the methods described herein.

Other possible vaccine formulations include oral and suppository formulations. Oral formulations commonly employ excipients (e.g., pharmaceutical grade sugars, saccharine, cellulose, and the like) and usually contain within 10–98% immunogenic polypeptide. Oral compositions take the form of pills, capsules, tablets, solutions, suspensions, powders, etc., and may be formulated to allow sustained or long-term release. Suppository formulations use traditional binders and carriers and typically contain between 0.1% and 10% of the immunogenic polypeptide.

In view of the above information, vaccines against BVDV-II can be generated which are composed of one or more structural or non-structural viral protein(s). These vaccines can contain recombinantly prepared BVDV-II polypeptides and/or polypeptides isolated from BVDV-II virions. In addition, it may be possible to prepare vaccines, which confer protection against BVDV-II infection through the use of inactivated BVDV-II. Such inactivation might be achieved by preparation of viral lysates followed by treatment of the lysates with appropriate organic solvents, detergents or formalin. Further, vaccines may be formulated to contain expression vectors capable of expressing a selected viral antigen (e.g., gp53) after injection into the tissues of the vaccinated animal.

The vaccines and immunological preparations of the present invention are administered in dosages compatible with the method of formulation, and in such amounts that will be pharmacologically effective for prophylactic or therapeutic treatments. The quantity of immunogen administered depends on the animal being treated, the capacity of the animal's immune system for antibody synthesis, and the desired level of protection. The amounts to be administered are usually determined by a qualified veterinary professional.

BVDV-II vaccines and immunological preparations of the present invention can be administered in single or multiple doses. Dosage regimens are also determined relative to the needs and tolerances of the animal to be treated. In addition to the BVDV-II immunogenic polypeptides, vaccine formulations may be administered in conjunction with other immunoregulatory agents, such as immunoglobins.

Further, the BVDV-II vaccines and immunological preparations of the present invention may be administered in combination with other vaccine agents, for example, with other pestivirus vaccines.

Composite vaccines designed to protect against several infectious agents may also be designed in accord with the present invention. An exemplary composite vaccine includes epitopes from both BVDV-I and BVDV-II antigens, and provides protection against all forms of BVDV. Such a vaccine may include, for example, both group I gp53 and group II gp53.

IX. Antibodies

In another aspect, the invention includes specific antibodies directed against polypeptide antigens of the present invention. Antigens (e.g., gp53) obtained by any of the methods described above may be used directly for the generation of antibodies, or they may be coupled to appropriate carrier molecules. Many such carriers are known in the art and are commercially available (e.g., Pierce, Rockford Ill.).

To prepare antibodies, a host animal, such as a rabbit, is typically immunized with the purified antigen or fused protein antigen. Hybrid, or fused, proteins may be generated using a variety of coding sequence derived from other proteins, such as glutathione-S-transferase or β-galactosidase (as described above). The host serum or plasma is collected following an appropriate time interval, and the serum is tested for antibodies specific against the antigen.

The gamma globulin fraction or the IgG antibodies of immunized animals can be obtained, for example, by use of saturated ammonium sulfate precipitation or DEAE Sephadex chromatography, affinity chromatography, or other techniques known to those skilled in the art for producing polyclonal antibodies.

Alternatively, purified antigen or fused antigen protein may be used for producing monoclonal antibodies. In this case, the spleen or lymphocytes from an immunized animal are removed and immortalized or used to prepare hybridomas by methods known to those skilled in the art (e.g., Harlow, et al.). Antibodies secreted by the immortalized cells are screened (e.g., using enzyme linked immunesorbent assay (ELISA) or a Western blot) to determine the clones that secrete antibodies of the desired specificity (e.g., Ausubel, et al.).

X. Diagnostic Methods

The present invention provides for methods to detect the presence of a BVD virus or portion thereof in a sample from a test animal. While the methods below discuss approaches to detecting primarily BVDV-II, it will be understood that by using appropriate BVDV-I polynucleotides, polypeptides, antibodies and the like, in combination with BVDV-II reagents, the diagnostic methods and kits may be utilized for the detection of both BVDV-I and BVDV-II (i.e., any BVD virus).

The present invention also provides for methods for the detection of anti-BVDV antibodies in a sample from a test animal. The presence of such antibodies indicates that the animal was previously infected by, or vaccinated against, a BVDV virus. The virus itself may or may not be present in such a sample.

It will be appreciated that, while the methods are discussed in reference to BVDV-II and cows, they may be also be applied to the detection of similar, heretofore unknown, diarrhea-causing viruses in other ruminants and in pigs.

A. Sources of Sample Material

The presence of a BVDV virus may be detected in an animal, such as a ruminant (e.g., cow or goat) or a pig, by obtaining a sample from the animal and testing the sample for evidence of a BVDV virus. The sample may comprise any suitable substance readily available from the animal, including blood, serum, leukocytes, saliva, and fecal material.

It will be understood that certain diagnostic methods may require specific sources of sample material. For example, diagnostics which test for the presence of anti-BVDV antibodies require a sample that is expected to contain antibodies (e.g., serum).

B. Nucleic-Acid-Based Diagnostic Methods

The nucleic acid sequences obtained by the methods of the present invention may be used as diagnostic agents for the detection of BVDV-II sequences present in a sample (e.g., serum), thereby indicating infection in the animal from which the sample was obtained. Primers and/or probes derived from the coding sequences of the present invention, in particular, BVDV-II gp53 (SEQ ID NO:1) can be used to detect BVDV-II.

In one diagnostic configuration, the sample is reacted under PCR or RT-PCR conditions using primers derived from, for example, BVDV-II gp53 sequences. The presence of BVDV-II, in the sample used in the amplification reaction, can be detected by specific amplification of the sequences targeted by the primers.

Alternatively, probes can be derived from the BVDV-II sequences of the present invention. These probes can then be labeled with reporter moieties and used as hybridization probes against nucleic acids present in a sample obtained from a test animal. The probes can be labeled using a variety of reporter molecules and detected accordingly: for example, radioactive isotopic labeling and chemiluminescent detection reporter systems (Tropix, Bedford, Mass.).

The labeled probes may be hybridized to samples being tested using standard hybridization procedures. Typically, polynucleotides isolated from a sample are immobilized on nylon or nitrocellulose membranes (e.g., Schleicher & Schuell, Keene, N.H.), the membranes are washed in a pre-hybridization solution and are then incubated at a controlled temperature in a hybridization solution containing the probe. Following hybridization, the membranes are washed under conditions effective to result in the desired degree of hybridization specificity. Such hybridization and wash conditions and procedures are well known in the art (e.g., Ausubel, et al., Sambrook, et al.).

The hybridization and wash conditions are preferably selected to achieve specific hybridization of probe molecules to BVDV-II sequences. For example, if a 1100 bp fragment encoding BVDV-II gp53 is used as a probe, standard high stringency wash conditions (Sambrook, et al.) are effective to result in specific hybridization of probe/pestivirus sequences, with a minimal amount of non-specific hybrids.

Rather than incorporating a reporter moiety or label directly into the probe used during the hybridization reaction, the probe may contain a tag or label that is specifically detected by a secondary reporter after completion of the hybridization reaction. For example, oligonucleotide probes may be fashioned to contain nucleotides derivatized with, for example, biotin or digoxigenin. These molecules may be detected after the hybridization reaction using streptavidin or anti-digoxygenin antibodies, respectively, linked to a secondary reporter, such as a fluorescent molecule or alkaline phosphatase. Methods for performing these operations are well known (e.g., Ausubel, et al.) and the reagents are widely available and may be conveniently obtained in the form of kits with detailed instructions (e.g., from Boehringer Mannheim, Indianapolis, Ind.).

Hybridized pestivirus/probe complexes (hybrids) may be detected using detection strategies appropriate for the reporter being employed. For example, if radiolabeled probes are used, membranes containing samples may be used to expose X-ray or photographic film (e.g., Kodak, Rochester, N.Y.). If the reporter includes an enzyme, such as alkaline phosphatase, the membrane is exposed to an appropriate substrate that allows visualization of the reaction product. The materials for many detection procedures are available in kits, which may be purchased from any of a variety of suppliers, including Boehringer Mannheim and Amersham Life Science (Arlington Heights, Ill.).

Also included in the invention is a diagnostic kit, which may include some or all of the components discussed in the above methods. Typically, such a kit contains lyophilized probe suitable for detecting BVDV-II nucleic acid sequences under specific hybridization conditions. The kit may also include a reaction support, a device for obtaining and dispensing a suitable sample, as well as reagents useful in the detection of probe-containing hybrids.

A variety of other amplification and detection methodologies may be employed in nucleic acid based BVDV-II diagnostics. A number of such techniques are known to the field of nucleic acid diagnostics (e.g., The 1992 San Diego Conference: Genetic Recognition, *Clin. Chem.* 39(4):705 (1993)).

C. Viral Antigen-Based Methods

Polypeptide antigens (e.g., gp53) obtained by the methods of the present invention may be employed as diagnostic reagents for the detection of antibodies present in the sera of animals infected with BVDV-II, thereby indicating infection in the animal. The antigens of the present invention can be used in order to detect BVDV-II or other closely-related viral agents.

In one diagnostic configuration, test serum from a pestivirus-infected ruminant or pestivirus-infected pig is reacted with a BVDV-II gp53 polypeptide antigen, and the antigen is examined for the presence of bound serum antibodies specifically immunoreactive with BVDV-II gp53 polypeptide antigen. The antigen may be attached, or immobilized on a solid support, and pre-incubated with a solution to reduce non-specific binding. The test serum may then be reacted with the support, and unbound serum components may be removed by washing. Antibodies present in the serum and directed against the immobilized antigen are captured on the support, and may be detected by subsequently reacting the support with a reporter-labeled detection antibody directed against the serum antibodies. For example, if a cow is being tested for the presence of anti-BVDV-II gp53 antibodies, the secondary antibody may be a goat anti-cow antibody.

The secondary antibody thus binds reporter to the support in proportion to the amount of bound anti-BVDV-II antibody. The support is again washed to remove unbound labeled antibody, and the amount of reporter associated with the support is determined using an appropriate method. For example, if the reporter is an enzyme, it may be detected by incubating the support in the presence of a suitable fluorometric or colorimetric substrate (Sigma, St. Louis, Mo.).

The polypeptide antigen is attached to the solid support in the above assay by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group.

Also forming part of the invention is an assay system or kit for carrying out this diagnostic method. The kit generally includes a support with surface-bound recombinant BVDV-II antigen (e.g., the BVDV-II gp53 antigen), a reporter-labeled secondary antibody (as above) for detecting surface-bound anti-BVDV-II antigen antibody, and may contain other reagents useful for visualizing the reporter-labeled secondary antibody.

In a second diagnostic configuration, known as a homogeneous assay, antibody binding to a solid support produces some change in the reaction medium which can be directly detected in the medium. Known general types of homogeneous assays proposed heretofore include (a) spin-labeled reporters, where antibody binding to the antigen is detected by a change in reported mobility (broadening of the spin splitting peaks), (b) fluorescent reporters, where binding is detected by a change in fluorescence efficiency or polarization, (c) enzyme reporters, where antibody binding causes enzyme/substrate interactions, and (d) liposome-bound reporters, where binding leads to liposome lysis and release of encapsulated reporter. The adaptation of these methods to the protein antigen of the present invention follows conventional methods for preparing homogeneous assay reagents.

In each of the assays described above, the assay method involves reacting serum from a test animal with the protein antigen and examining the antigen for the presence of bound antibody. The examining may involve attaching a labeled secondary antibody (directed against the animal being tested) to the antibody being examined and measuring the amount of reporter bound to the solid support, as in the first method, or may involve observing the effect of antibody binding on a homogeneous assay reagent, as in the second method.

D. Antibody-Based Methods

Another diagnostic configuration involves use of BVDV-II antibodies capable of detecting BVDV-II-specific antigens. A sample which may contain BVDV-II-specific antigens is contacted with a substantially purified anti-BVDV-II antibody, such as an anti-gp53 antibody. The antibody is then examined for the presence of bound antigen.

The antibody may be bound to a solid substrate, incubated with a blocking solution, and contacted with a sample to be tested. If the sample contains BVDV-II viral antigens, the antigens are captured by the immobilized antibody, and may be detected by a second, labeled anti-BVDV-II antibody. Typically, the captured antigens comprise viral particles, which may then be detected using any secondary antibody that specifically reacts with the virus. The secondary antibody may the same as the immobilized antibody (e.g., anti-BVDV-II gp53 antibody), since the captured particle typically contains numerous copies of the target antigen, some of which are exposed and available for the secondary reaction.

The amount of captured antigen may also be quantitated by determining the fraction of immobilized antibody sites not occupied by antigen captured from the serum sample. In this variation, a solution containing reporter-labeled antigen specifically immunoreactive with the immobilized antibody is contacted with the support after the support is exposed to the sample. Immobilized antibodies that did not capture antigen from the sample are free to react with the labeled antigen. The amount of captured labeled antigen is detected as above, and is inversely proportional to the amount of antigen present in the serum sample.

Antibodies can be prepared, utilizing the peptides of the present invention, by standard methods (Harlow, et al.). Substantially isolated antibodies (essentially free of serum proteins which may affect reactivity) can also be generated using standard methods (e.g., affinity purification (Harlow, et al.)).

Also included in the invention is a diagnostic kit for use with the above detection methods. Such a kit typically contains a solid support with immobilized anti-BVDV-II antibody, and, depending on the variation employed, either a reporter-labeled secondary antibody or a labeled antigen specifically immunoreactive with the immobilized antibody.

The following examples illustrate but in no way are intended to limit the present invention.

MATERIALS AND METHODS

A. Cells and Viruses

Madin Darby bovine kidney (MDBK) cells, BSC-1 cells, and bovine turbinate (BT) cells were obtained from the American Type Culture Collection (ATCC; Rockville, Md.). The MDBK cells, cultured in MEM (Gibco/BRL, Gaithersburg, Md.) supplemented with 10% horse serum (Gibco/BRL) and gentamicin (25 µg/ml) in a $CO_2$ incubator, were used for Bovine Viral Diarrhea Virus (BVDV) propagation. BSC-1 cells were cultured under the same conditions but horse serum was replaced with fetal bovine serum. Cell lines and media used for cell culture were free of contaminating BVDV.

Wild-type vaccinia virus (WR strain), obtained from the American Type Culture Collection (ATCC; Rockville, Md.), and vaccinia recombinants were propagated in BSC-1 cells. Conditions for secretion of proteins in heat-shocked (6 hours at 43° C.) gp53-transfected MDBK cells were as described previously (Kowalski, et al., 1993). Briefly, the cultures were washed twice to remove serum and incubated at 43° C. in a minimal volume (10 ml/150 $cm^2$) of serum-free MEM or "OPTIMEM I" (Gibco). Production of gp53 was induced by increasing the incubation temperature to 43° C. for 6 hours, after which the cells were incubated at 37° C. for a period of 18 to 96 hours. At the end of the incubation period, the medium was collected and centrifuged for 5 minutes at 2000 g to remove cells and debris, and analyzed for the presence of soluble protein as described below.

BVDV field isolates listed in Table 1, below, were selected from different regions in North America. Isolates Q47, Q69, Q126, Q140, Q713, Q1111, Q1808, Q2101, and Q4812 were obtained from the Ministère de l'Agriculture, des Pêcheries et de l'Alimentation du Québec (MAPAQ) at Institut Armand-Frappier (Laval, Québec, Canada). Isolates 1854, 1494, Waters, Bull, C1, and C3 were collected from cattle by the veterinary Infectious Disease Organization (VIDO; University of Saskatchewan). The field isolates were propagated on MDBK or BT cells for a maximum of two passages and were not cloned.

TABLE 1

| Strain | Characteristics | Origin |
| --- | --- | --- |
| Q1111[a] | Veal calf | Quebec |
| Q1808 | Immunotolerant calf | Quebec |
| Q69 | Aborted fetus | Quebec |
| Q126[a] | Veal calf | Quebec |
| Q4812[a] | Veal calf | Quebec |
| Q47 | Adult with dehydration | Quebec |
| Q713 | Veal calf | Quebec |
| Q2101[a] | Veal calf | Quebec |
| Q140[a] | Nursing calf | Quebec |
| Waters | Immunotolerant adult | Saskatchewan |
| C1 | Dead from mucosal disease | Saskatchewan |
| C3 | Dead from mucosal disease | Saskatchewan |
| 1854 | Immunotolerant adult | Saskatchewan |
| 1494 | Dead from mucosal disease | Saskatchewan |
| Bull | Immunotolerant adult? | Alberta |
| CD87 | Thrombocytopenia | United States |
| 890 | Thrombocytopenia | United States |

[a]Associated with severe outbreaks in Quebec.

BVDV laboratory strains NADL, NY-1, Singer, Draper, and Oregon were obtained from the National Veterinary Service Laboratories (NVSL; Ames, Iowa) and were cloned prior to use by limiting dilution on the MDBK cells. Strains CD87 and 890 were provided by Drs. E. J. Dubovi (Cornell University, Ithaca, N.Y.; Corapi, et al., 1989) and S. R. Bolin (United States Department of Agriculture—USDA/ARS, Ames, Iowa; Bolin and Ridpath, 1992), respectively. Both CD87 and 890 are thrombocytopenic strains.

BVDV isolates were propagated and titered in BVDV-free MDBK cells maintained in MEM supplemented with 10% horse serum and antibiotics as described above. Virus stocks, obtained from infected cells, were aliquoted and stored at −70° C. Virus titers were determined in 96-well microtiter plates using MDBK cells as described below.

B. gp53 Expression Vectors

MDBK cells were infected with the NADL strain of BVDV at 10 pfu/cell. At 52 hours post-infection total cytoplasmic RNA was prepared as described previously (Kowalski and Denhardt, 1989). First strand cDNA was synthesized using 5 µg RNA and M-MLV reverse transcriptase deficient in RNase H ("SUPERSCRIPT", Gibco/BRL, Gaithersburg, Md.). The reaction was treated with 1 mg/ml RNase A and the reaction products were purified by adsorption to glass beads ("GENE-CLEAN", Bio 101, La Jolla, Calif.) following the manufacturer's instructions.

1. Full-Length gp53 in Vaccinia Virus

Figure 7:
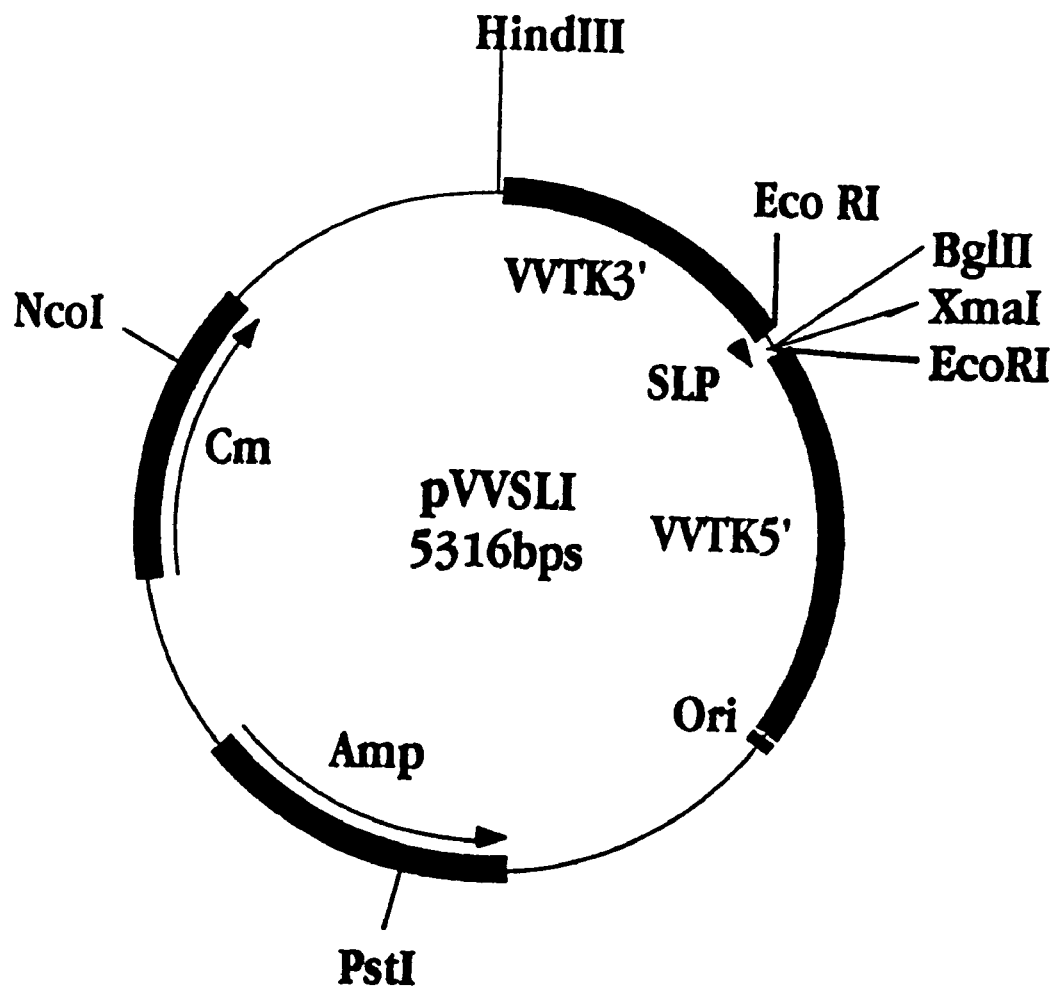
FIG. 7 shows a schematic map of plasmid pVVSLI.
Figure 8:
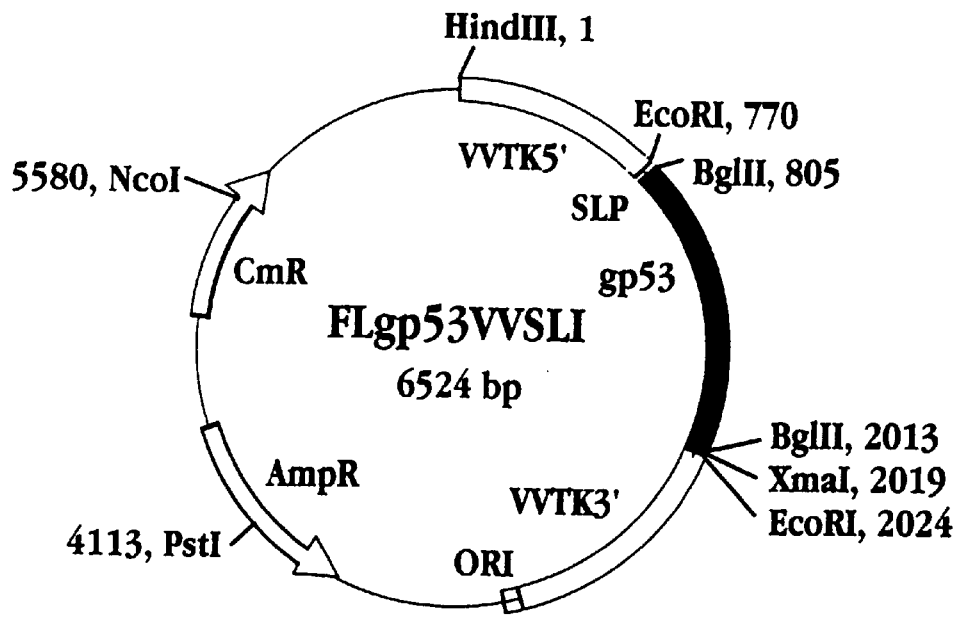
FIG. 8 shows a map of plasmid pFLgp53VVSLI.

Polymerase chain reaction (PCR; Mullis; Mullis, et al.,) primers 1A (SEQ ID NO:10) and 1B (SEQ ID NO:11) were designed to amplify a polynucleotide fragment encoding a full length gp53 (FLgp53) of the NADL open reading frame (Collett, et al., 1988a), flanked by in-frame translational start and stop codons. The primers contained sequences that resulted in the addition of BglII cleavage sites at the ends of the PCR products. PCR was carried out using Vent polymerase (New England Biolabs, Beverly, Mass.). Amplified PCR product was purified using agarose gel electrophoresis, digested with BglII, and cloned into the unique BglII site of pVVSLI (FIG. 7; Tikoo, et al., 1993). The resulting vaccinia transfer plasmid, designated pFLgp53VVSLI is shown in FIG. 8. The symbols on the map of the vector are as follows: VVTK5' and VVTK3' are the Vaccinia thymidine kinase gene 5' and 3' portions SLP is the synthetic late promoter; pg53 is a fragment encoding a full-length gp53; ORI is the origin of plasmid replication in E. coli; AmpR is the E. coli β-lactamase gene; and CmR is a chloramphenicol resistance gene. Arrows denote direction of transcription.

2. Truncated gp53 in MDBK Cells

Figure 9:
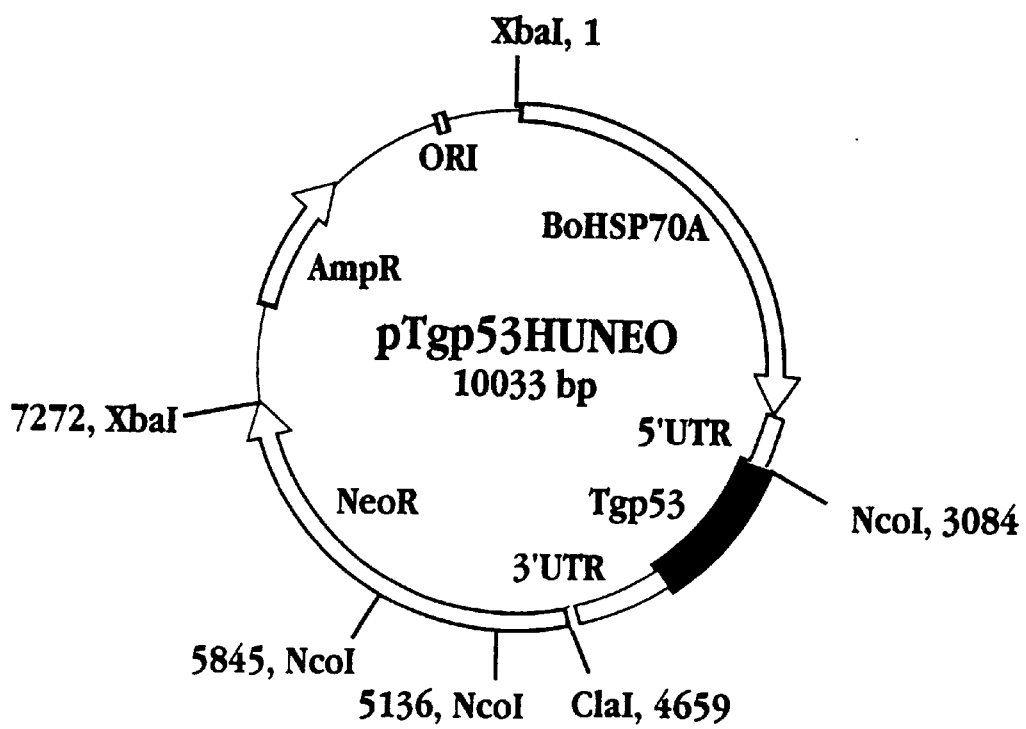
FIG. 9 shows a map of plasmid pTgp53HUNEO.

For expression in the hsp70 promoter-driven MDBK cell system, a DNA fragment encoding amino acids 666 (Leu) to 1036 (Ile) of NADL gp53 (Collett, et al., 1988a) was amplified using PCR as above. The upstream primer (2A; SEQ ID NO:12) contained an NcoI site, while the downstream primer (2B; SEQ ID NO:13) contained a SalI site after a translational stop codon. Following digestion with NcoI and SalI the PCR product was inserted between the NcoI and XhoI sites of pG$_4$HUNEO (Kowalski, et al., 1993), generating pTgp53HUNEO (FIG. 9). In FIG. 9, the symbols are as follows: BoHSP70A is the bovine hsp70 gene transcriptional promoter; 5'UTR is the 5'-untranslated region of bovine hsp70 mRNA; gp53t is a fragment containing a truncated gp53 open reading frame; 3'UTR is the 3'untranslated region of human hsp70 gene; NeoR is the aminoglycoside phosphotransferase gene under SV40 control; AmpR is the E. coli β-lactamase gene; and ORI is the origin of plasmid replication in E. coli. As above, arrows denote the direction of transcription.

3. Truncated gp53 in Vaccinia Virus

A polynucleotide encoding the truncated form of gp53 (Tgp53) was obtained from pFLgp53VVSLI (above vector) by PCR. The 5'-end primer was primer 1A (SEQ ID NO:10), and the 3'-end primer was primer 2B (SEQ ID NO:13). A SalI to BglII adaptor was used to insert the PCR product into the BglII site of pVVSLI (FIG. 7; Tikoo, et al., 1993). The resulting plasmid was designated Tgp53VVLI.

C. Expression of Full-Length and Truncated gp53

Vaccinia transfer vectors were inserted into vaccinia virus (WR strain) and recombinant viruses were selected as described previously (Tikoo, et al., 1993).

Briefly, the recombinant vaccinia vectors were made by homologous recombination by electroporation of linearized plasmid DNA into wild-type vaccinia virus-infected LMTK⁻ (thymidine kinase-negative) cells using a Pharmacia Gene Pulser (Pharmacia Biotech, Piscataway, N.J.) at 200 V and 500 µF. The recombinant vaccinia viruses were identified by screening TK⁻ plaques for expression of recombinant proteins by immunocytochemistry (immunoperoxidase staining as described below). Plaque-purified vaccinia virus recombinants with FLgp53 (FLgp53VV#41) and Tgp53 (Tgp53VV#51) were selected.

MDBK cell lines expressing truncated gp53 (Tgp53) were constructed by liposome-mediated transfection ("LIPOFECTIN", Gibco/BRL, Gaithersburg, Md.) with the pTgp53G4HUNEO vector described above. Cell lines were isolated by growing in the presence of 666 µg/ml G418 (Gibco/BRL) as described previously (Kowalski, et al., 1993) and cloned twice to ensure clonal purity. Secreted Tpg53 of clone #60 was used for further characterization.

D. Purification by Affinity Chromatography

NADL strain glycoprotein 53 (gp53) was purified by immunoaffinity chromatography using monoclonal antibodies specific for BVDV gp53. The IgG fraction of the gp53 monoclonal antibody 450-19 (obtained from Dr. D. Deregt, ADRI (Animal Disease Research Institute), Lethbridge, Alberta, Canada; Deregt, et al., 1990) was prepared from ascites fluid, using a protein A conjugated "SEPHAROSE CL4B" (Pharmacia Biotech, Montreal, Canada) column.

The purified IgG was dialyzed against 0.1 M NaHCO$_3$, linked to activated "AFFI-GEL 10" (BioRad, Mississauga, Ontario, Canada) at a concentration of 5 mg/ml according to the manufacturer's instructions, and packed into a column.

gp53 was purified from full length gp53 recombinant vaccinia virus (FLgp53VV#41)-infected BSC-1 infected cells, from cell culture media of truncated gp53 recombinant vaccinia virus (FLgp53VV#41) BSC-1 cells, and from cell culture media of heat-shocked transfected MDBK cells (Tgp53MDBK#6).

Full length gp53 was extracted from infected BSC-1 cells as follows. The cells were harvested, centrifuged at 2,000 rpm for 10 minutes in 10 mM Tris-HCl, 150 mM NaCl, pH 7.5, containing 1% Nonidet P40 ("NP40") and 1% deoxycholate (DOC), and the supernatant from this low-speed spin was subjected to ultracentrifugation for one hour at 30,000 rpm. The supernatant obtained from the ultracentrifugation was used for affinity chromatography as described below.

Secreted, truncated gp53 was purified from the supernatants of cell culture media of Tgp53VV#51-infected BSC-1 cells or Tgp53-transfected MDBK cells (Tgp53MDBK#60) after removal of cellular debris by centrifugation at 2000 rpm for 10 minutes. Further purification of the gp53-containing supernatants was by subjecting them to affinity chromatography as described below.

Supernatants containing FLgp53 or Tgp53 were each passed through their affinity column three times. After washing unbound material from the columns with 10 mM Tris-HCl, 500 NaCl, 0.1% "NP40", pH 7.5, bound protein was eluted with 50 mM diethylamine, pH 11.5, and neutralized with Tris-HCl. The eluted proteins were concentrated on an Amicon (Danvers, Mass.) YM10 membrane filter, and dialyzed against phosphate-buffered saline (PBS). The protein concentration was determined with a BioRad protein kit (BioRad Laboratories, Mississauga, Ontario, Canada), and the purity of the proteins was assessed by PAGE and Western blotting as described above.

E. PAGE Analysis and Western Blots

The BVDV proteins were analyzed by sodium dodecyl sulfate (SDS)-polyacrylamide gel electrophoresis (PAGE) on 10% discontinuous gels under reducing and non-reducing conditions. Specific proteins were visualized using the Western blotting technique of Burnette. Following electrophoresis, cell lysates, cell culture medium, or purified glycoproteins were electrophoretically transferred to nitrocellulose membranes. The presence of gp53 in the samples was analyzed following incubations of the membranes with gp53-specific monoclonal antibody mixture (19F7 ascites provided by Dr. E. Dubovi, Cornell, Ithaca, N.Y. (Donis, et al., 1988), and 157-77, 348-14, 450-19, and 477-71 ascites provided by Dr. D. Deregt, Animal Disease Research Institute, Lethbridge, Alberta (Deregt, et al., 1990), diluted 1:400 goat anti-mouse horseradish peroxidase conjugate, and chromogen (Immunoblot Assay Kit, BioRad, Mississauga, Ontario, Canada), following the manufacturer's instructions.

F. gp53 ELISA

An indirect ELISA was used for the quantitation of gp53 produced in the expression systems described above. "IMMUNLON II" 96-2311 microtiter plates (Dynatech Laboratories, Alexandria, Va.) were coated with serial twofold dilutions of antigen samples or Tgp53 standards in 0.05 M Na-carbonate buffer, and the plates were left overnight at room temperature. The monoclonal antibody cocktail consisted of equal amounts of 19F7, 157-77, 348-14, 450-19, and 477-71 ascites fluid (1:400 dilutions). Samples of 19F7 ascites were obtained from Dr. E. Dubovi (Cornell University, Ithaca, N.Y.; Donis, 1988), and samples of 157-77, 348-14, 450-19, and 477-71 ascites were obtained from Dr. D. Deregt (ADRI, Lethbridge, Alberta, Canada).

After washing with PBS-T (140 mM NaCl, 3 mM KCl, 8 mM $KH_2PO_4$, 0.05% "TWEEN 20", pH 7.2; all chemicals from Sigma Chemical Co., St. Louis, Mo.), the plates were incubated with horseradish peroxidase-conjugated goat anti-mouse IgG (1:10,000); Boehringer Mannheim, Dorval, Quebec, Canada). After washing of the plates with PBS-T, chromogen containing 5-aminosalicylic acid (0.08%) and $H_2O_2$ (0.005%) was added to the plates for visualization of the reaction. The absorbance at 492 nm was measured and the concentration of Flgp53 and Tgp53 were determined from a standard curve of pure Tgp53.

G. BVDV Antisera

Polyvalent antisera against BVDV strains were generated by infection of animals with live virus. The animals were infected with $5*10^7$ tissue culture infectious dose 50 ($TCID_{50}$; the highest dilution of a virus-containing solution that produces infection in 50% of the cell cultures inoculated; measured on MDBK cells) of BVDV. Serum was collected 4 weeks after immunization.

Antisera against CD87 and NY-1 were raised in BVDV-free lambs by intratracheal inoculation while the antiserum against the NADL strain was generated in a BVDV-free caesarean-derived colostrum-deprived piglet kept in an isolation facility by intravenous inoculation. Anti-Waters serum came from a cow infected with the virus. The anti-NADL serum was also used for immunocytochemical detection.

Monospecific serum against gp53 was obtained from rabbits that were immunized twice with 10 μg affinity-purified FLgp53 or Tgp53 from recombinant vaccinia virus infected cells or gp53 transfected MDBK cells (see above). The proteins were mixed with avridine (Molecular Genetics, Inc., Minnetonka, Minn.) as an adjuvant and administered intramuscularly twice, with an interval of three weeks.

Serum was isolated from whole blood by centrifuging for 20 minutes at 2000 rpm in a table-top clinical centrifuge.

H. Immunoperoxidase Staining

The presence of gp53 in cells was determined by an indirect immunochemical detection method (Bielefeldt-Ohmann, et al., 1987). Cells cultured in microtiter plates were washed with saline (140 mM NaCl), dried at 37° C. for 2 hours, and fixed by incubating in an acetone-saline mixture (20% by volume acetone in saline) for 10 minutes.

After drying as above, the plates were washed with saline, and incubated with either porcine anti-BVDV (NADL strain) or gp53-specific monoclonal antibody mixture, as above, in serum diluent (29.5 g NaCl, 10.0 g "TWEEN 80", 1.0 g $NaN_3$ per liter $ddH_2O$, pH 7.6) for 1 hour at room temperature (monoclonal antibodies were used for demonstration of gp53 production in gp53-recombinant vaccinia virus infected cells and in gp53-transfected MDBK cells).

Following 3 washes with wash fluid (8.85 g NaCl and 5.0 g "TWEEN 80" per liter, pH 7.6), the plates were incubated with either rabbit anti-mouse peroxidase conjugate or goat anti-mouse IgG peroxidase conjugate (Sigma Chemical Co., St. Louis, Mo.) in conjugate diluent (29.5 g NaCl and 10.0 g "TWEEN 80" per liter, pH 7.6) for 1 hour. Following 3 washes as above, the cells were incubated with substrate solution containing 0.04% 3-amino-9-ethylcarbazole and 0.02% $H_2O_2$ in 0.05 M sodium acetate buffer, pH 5.0 (all chemicals from Sigma Chemical Co., St. Louis, Mo.). A red cytoplasmic coloration of the cells observed by light microscopy, indicated the presence of gp53 in the cells.

I. Virus Neutralization (VN) Assay

Serial twofold dilutions of serum were made in MEM supplemented with 10% horse serum and gentamicin (as above). The dilutions ranged from 1:2 to 1:100,000 (serum:MEM). The serum-containing MEM mixtures were combined with an equal volume of culture medium containing about 100 $TCID_{50}$ units of a selected strain of BVDV. After an incubation of one hour at 37° C. and 5% $CO_2$ in an incubator, the mixture was transferred to 96 well plates containing MDBK cells.

Following a further incubation of three days in a 5% $CO_2$ in an incubator, the plates were washed with saline and dried for 2 hours as before. The presence of BVDV in the cells was determined by indirect immunocytochemistry (see above). The virus neutralizing titer (VN) was the reciprocal of the highest serum dilution giving a 100-fold reduction in VN titer. VN tests were carried out in quadruplicate.

EXAMPLE 1

Virus Neutralization Using Group-Specific Sera Raised by Infecting Animals with BVDV Sera against BVDV isolates NADL, NY-1, CD87 and Waters, were obtained as described above (Materials and Methods; section G). The virus neutralization titers of each serum sample were determined against the Draper, NADL, NY-1, Oregon, Singer, CD87, Waters, 890 and 1494 isolates of BVDV as described above (Materials and Methods; section I).

Results from these experiments are shown in Table 2, below. The reactivity patterns fall into two groups (termed BVDV Group I and BVDV Group II). While some differences in VN titers were observed within each group, the neutralization titers of sera obtained from animals infected with group I strains were at least four-fold higher against group I isolates than group II isolates, and vice versa.

TABLE 2

COMPARISON OF BVDV VN TITERS AGAINST THE BVDV STRAINS

| Virus Strain | BVDV VN Titers in Sera from Animals Infected with: | | | |
|---|---|---|---|---|
| | NADL | NY-1 | CD87 | Waters |
| Group I | | | | |
| Draper | 3200 | 6400 | 200 | 1600 |
| NADL | 12800 | 3200 | 200 | 800 |
| NY-1 | 2400 | 4800 | 100 | 600 |
| Oregon | 3200 | 6400 | 100 | 800 |
| Singer | 2400 | 2400 | 100 | 1600 |
| Group II | | | | |
| CD87 | 50 | 50 | 6400 | 12800 |
| Waters | 200 | 100 | 12800 | 51200 |
| 890 | 200 | 200 | 25600 | 25600 |
| 1494 | 200 | 200 | 12800 | 25600 |

Note that the VN titers of sera from animals infected with NADL and NY-1 are significantly higher against the panel of isolates listed in the top part of the Table (group I) than against isolates listed in the bottom part of the table (group II). Similarly, VN titers of sera from animals infected with CD87 and Waters are higher against the group II strains than against the group I strains.

These results suggest that while some neutralizing antibodies may cross-react between strains from different groups, the best consistent protection against a particular target strain is afforded by neutralizing antibodies from sera of animals infected with a strain from the same group (i.e., either BVDV Group I or BVDV Group II) as the target strain.

EXAMPLE 2

Virus Neutralization Using Group-Specific Sera Against gp53 Raised in Rabbits

Rabbit sera against affinity-purified FLgp53 or Tgp53 (NADL strain) were obtained as described above (Materials and Methods; section G). The VN titers of the sera were determined against several BVDV Group I and Group II isolates. Group I (BVDV-I) isolates included C1, C3, Draper, NADL, NY-1, Oregon, Singer, 1854, Q1808, Q69, Q47, Q713. Group II (BVDV-II) isolates included CD87, Waters, 890, 1494, Q1111, Q126, Q140, Q2101, Q4812. The isolates were obtained as described above in Materials and Methods.

The results from these experiments are shown in Table 3, below.

TABLE 3

BVDV NEUTRALIZING TITERS IN RABBITS IMMUNIZED WITH GP53 (NADL STRAIN)

| BVDV | | BVDV VN Titers of Rabbits Immunised with[a] | | |
|---|---|---|---|---|
| Virus Isolate | Character-istics | FLgp53 Vaccinia | Tgp53 Vaccinia | Tgp53 MDBK Cells |
| Group I | | | | |
| C1 | MD | 12,000 | 48,000 | 24,000 |
| C3 | MD | 12,000 | 36,000 | 24,000 |
| Draper | LAB | 12,000 | 96,000 | 16,000 |
| NADL | LAB | 36,000 | 96,000 | 48,000 |
| NY-1 | LAB | 12,000 | 96,000 | 24,000 |
| Oregon | LAB | 24,000 | 48,000 | 48,000 |
| Singer | LAB | 24,000 | 48,000 | 48,000 |
| 1854 | PI | 12,000 | 32,000 | 32,000 |
| Q1808 | QUE | 24,000 | 96,000 | 24,000 |
| Q69 | QUE | 12,000 | 24,000 | 24,000 |
| Q47 | QUE | 24,000 | 24,000 | 24,000 |
| Q713 | QUE | 36,000 | 48,000 | 16,000 |
| Group II | | | | |
| CD87 | Thromb. | 1,000 | 4,000 | 1,000 |
| Waters | PI | 1,000 | 4,000 | 1,000 |
| 890 | Thromb. | 1,000 | 4,000 | 1,000 |
| 1494 | PI | 750 | 4,000 | 1,000 |
| Q1111 | QUE | 500 | 2,000 | 1,000 |
| Q126 | QUE | 500 | 4,000 | 1,000 |
| Q140 | QUE | 500 | 2,000 | 500 |
| Q2101 | QUE | 750 | 4,000 | 1,000 |
| Q4812 | QUE | 750 | 2,000 | 500 |

[a]Mean BVDV neutralizing antibody titers in sera of 2 rabbits after 2 immunizations with affinity purified gp53.
[b]Thromb: thrombocytopenia; LAB: laboratory strain; Resp: respiratory disease; PI: persistent infection; QUE: Quebec isolate.

The results shown in Table 3 illustrate that FLgp53 as well as Tgp53 from a group I BVDV strain (NADL) are effective at neutralizing viral infectivity of other group I isolates, but are at least 9-fold less effective at neutralizing infectivity of group II BVDV isolates. These results suggest that the gp53 protein of group I strains is different enough from the gp53 protein of group II strains that the majority of neutralizing antibodies raised against one of the proteins do not cross-react with the other. Accordingly, an immunological preparation, such as a vaccine, raised against group I gp53 proteins would not be expected to be very reactive with group II gp53 proteins. By extension, such a vaccine would not be expected to be very effective against group II BVDV isolates.

EXAMPLE 3

Virus Neutralization Using Group-Specific Sera Against gp53 Raised in Calves

Two groups of six, one-year old beef calves, all negative for BVDV antibody and virus, were immunized twice intramuscularly, 21 days apart. The calves in the first group received 100 μg affinity purified FLgp53 produced in recombinant FLgp53-vaccinia virus infected BSC-1 cells, and those in the second group received 100 μg affinity purified Tgp53 produced in Tgp53-transfected MDBK cells, all in VSA3 adjuvant (Biostar, Saskatoon, SK, Canada). Two weeks after the second immunization, blood samples were taken from the calves for BVDV VN antibody analysis in the sera.

The data, shown in Table 4, below, confirm the results obtained with the rabbit sera (Example 2). Sera from calves immunized with gp53 from NADL (group I BVDV) neutralize group I BVDV over ten times more effectively than group II BVDV.

TABLE 4

BVDV NEUTRALIZING TITERS IN CALVES IMMUNIZED
WITH GP53 (NADL STRAIN)

| BVDV Isolate | Group | BVDV VN Titers of calves Immunized with[1] | |
|---|---|---|---|
| | | FLgp53 Vaccinia | Tgp53 MDBK Cells |
| NADL | I | 20,008 | 5,161 |
| NY-1 | I | 14,596 | 2,294 |
| 890 | II | 1,290 | 203 |
| 1494 | II | 813 | 102 |

[1]Geometric mean BVDV neutralizing antibody titers in sera from 6 calves after 2 immunizations with affinity purified gp53.

EXAMPLE 4

Molecular Cloning of BVDV-II gp53

A. RNA Extraction

Viral RNA from strain 1494 was extracted from the supernatants of MDBK cells infected with the 1494 virus using the guanidinium isothiocyanate method described by Chomczynski and Sacchi (1987).

Briefly, 10 ml of cell culture medium from 5-day old virus-infected MDBK culture, clarified by centrifugation for 10 minutes at 2000 rpm in a clinical centrifuge, was concentrated by an ultracentrifugation for 2 hours at 40,000 rpm (150,000× g; SW50.1 rotor in Beckman L3-50 ultracentrifuge, Beckman Instruments, Inc., Fullerton, Calif.), and virus-containing pellets were resuspended in 500 µl PBS. 150 µl of the concentrated virus/PBS solution was mixed with 500 µl denaturing solution (4 M guanidinium thiocyanate, 25 mM sodium citrate, pH 7, 0.1 M 2-mercaptoethanol and 0.5% N-lauroylsarcosine) and transferred into a 1.5-ml Eppendorf polypropylene tube. 50 µl of 2 M sodium acetate, pH 4, was added and the mixture was mixed thoroughly by inversion. 0.5 ml of water-saturated phenol was then added, the mixture was again mixed, and 0.1 ml of 49:1 chloroform/isoamyl alcohol were added, followed by another mixing and incubation for 15 min at 0–4° C.

Following the incubation, the mixture was centrifuged for 20 min in a microcentrifuge (14,000× g), 4° C., and the upper aqueous phase, containing RNA, was transferred to a fresh tube. The RNA was precipitated by adding 1 volume of 100% isopropanol and placing the samples for 2 hours at –20° C. The samples were then centrifuged for 10 min at 10,000× g, 4° C. to pellet the RNA. The RNA pellet was then dissolved in 0.15 ml denaturing solution, and precipitated again with 1 volume of 100% isopropanol and a 30 min incubation at –20° C. The samples were again centrifuged as above.

The pelleted RNA was washed with 75% ethanol, air-dried, and dissolved 60 µl DEPC-treated water.

B. Primers

Primer $BV_{II}$ (SEQ ID NO:3), primer pII-350 (SEQ ID NO:4), and primer pII-251 (SEQ ID NO:5) were synthesized using a Gene Assembler Plus (Pharmacia, Piscataway, N.J.). The primer sequences were chosen based on the sequence of the NADL gp53 sequence (Collett, et al., 1988a).

C. Reverse Transcription

Viral RNA, obtained as described above, was reverse transcribed to generate first-strand cDNA polynucleotides using standard methods (Sambrook, et al.). Briefly, the reverse transcriptase (RT) reactions were performed by adding 1 µl of $BV_{II}$ (SEQ ID NO:3) or PII-350 (SEQ ID NO:4) primer (50 pmol/µl), 1 µl of a 10 mM dNTP mix (Boehringer Mannheim, Indianapolis, Ind.), 2 µl of 10× RT buffer (200 mM Tris-HCl (pH 8.4), 500 mM KCl, 25 mM $MgCl_2$, 0.1 M dithiothreitol, 1 mg/ml BSA), 1 µl of RNase inhibitor RNAguard (20 U/µl; Pharmacia Biotech, Piscataway, N.J.), and 9 µl DEPC-treated water to 5 µl of viral RNA. This mixture was heated for 15 minutes at 65° C., placed on ice and 0.5 µl of MMuLV-RT (20 U/µl; Pharmacia Biotech) were added. The reaction was carried out at 42° C. for 30 min, an additional 10 units of MMuLV-RT were added and the reaction was continued for another 30 min. Reaction products (first strand cDNA) were immediately used for PCR or stored at –20° C.

D. Polymerase Chain Reaction

Reaction products from the reverse transcription reaction (above) were added to 80 µl of PCR mix (50 pmol of the $BV_{II}$ (SEQ ID NO:3) or PII-350 (SEQ ID NO:4) primer, 100 pmol of the PII-251 (SEQ ID NO:5) primer, 10 mM Tris-HCl (pH 9.0), 50 mM KCl, 3 mM $MgCl_2$, and 0.1% "TRITON X-100"). The resulting mixture was overlaid with 80 µl of light mineral oil, heated at 95° C. for 5 min, and left to cool at 72° C. before 1.5 U of Taq DNA polymerase were added.

The mixture was placed in a DNA Thermal Cycler Model 480 (Perkin-Elmer, Emeryville, Calif.) and subjected to 35 cycles of thermal cycling. Each cycle consisted of 1 min at 94° C. (denaturation), 1.5 min at 50° C. (annealing), and 2.5 min at 72° C. (elongation). The final cycle was followed by a 10-min extension at 72° C.

E. Cloning of PCR Products

PCR products were ligated into the PCRII vector (Invitrogen, San Diego, Calif.) according to the manufacturer's instructions. This vector is sold in linear form with single 3' "A" overhangs at the ends to facilitate direct cloning of PCR products. The vector also contains the lacZa complementation fragment for blue-white color screening and ampicillin and kanamycin resistance genes for selection.

Ten percent (1 µl) of the ligation product was used to transform competent XL1-Blue cells (Stratagene, La Jolla, Calif.) according to standard calcium chloride heat-shock transformation methods (Sambrook, et al.).

Aliquots of the transformation mixture were plated on 150 mm Luria Broth (LB; Sambrook, et al.) agar plates (containing 50 µg/ml ampicillin and spread with 50 µl 40 mg/ml 5-bromo-4-chloro-3-indolyl-D-galactoside (Xgal)

F. Sequencing and Analysis

Four white clones were selected and inserts were sequenced using the dideoxy method (Sanger, et al., 1977) with the AutoRead sequencing kit (Pharmacia Biotech) and the Automated Laser Fluorescent (ALF) DNA sequencer (Pharmacia Biotech).

The nucleotide sequence of a portion of the 1494 viral genome encoding gp53 is presented as SEQ ID NO:1 and shown in FIG. 1. The translated amino acid sequence is presented as SEQ ID NO:2 and shown in FIG. 2.

The nucleic and amino acid sequences disclosed herein corresponding to BVDV-II gp53 are compared to those of several other pestivirus isolates in FIG. 3 (nucleotide sequence comparison) and FIG. 4 (amino acid sequence comparison). The beginning and end of sequences encoding gp53 are also graphically indicated in FIGS. 3 and 4. The first (5') portion of the sequences presented in the Figures corresponds to the end of gp47, the main portion corresponds to gp53, and the last (3') portion corresponds to the beginning of p54. The sequences are aligned in both FIGS. 3 and 4 as follows. Line 1 corresponds to the gp53 sequence of the Osloss isolate (O), line 2 to the NADL isolate (N), line 3 to the BD-78 (B) isolate, and line 4 to the 1494 Saskatoon Isolate cloned and sequenced as described above. Line 5 in FIG. 4 corresponds to the X818 (X) isolate of border virus (Becher, et al.).

The sequences were analyzed on an IBM-compatible PC computer using the "CLUSTAL" program from the PC/GENE (IntelliGenetics, Inc., Mountain View, Calif.) suite of programs. "CLUSTAL" parameters were set to the default values. This program analyzes groups of sequences for their similarity to one another and presents the results in the form of a dendogram. The lengths of the arms of the dendogram reflect the degree of similarity among the sequences—shorter arms separating two sequences indicate that the sequences are similar, while longer arms indicate that they are more divergent.

The results of a "CLUSTAL" analysis of gp53 amino acid sequences from BVDV group I isolates Osloss (OSP) and NADL (NAP), BVDV group II isolate 1494 (14P), border disease virus (BDV) isolates X818 (X8P) and BD-78, and hog cholera virus (HoCV) isolate Alfort (ALP), as well as the sequence alignments presented in FIGS. 3 and 4, indicate that (i) BVDV-II strain 1494 is closely related to the BD-78 border disease virus (~90% homology at the amino acid level), but not to other border disease viruses, such as X818; (ii) BVDV-II strain 1494 is different from group I BVDV strains, such as Osloss and NADL (60–70% amino acid homology); and (iii) Alfort hog cholera virus is closely related to X818 border disease virus, and both are more similar to group I BVDVs than to group II BVDVs.

The similarity of 5' UTR sequences among various BVDV-II strains, described in Example 5 below, suggests that conclusions drawn above for strain 1494 may be generalized to all BVDV-II strains.

EXAMPLE 5

Molecular Cloning of a BVDV-II 5' Untranslated Region

Viral RNA was purified from culture media of cells infected with strains Singer, Oregon, C3, C1, NY-1, Draper, Q47, Q713, Q69, Q1808, 1854, 890, CD87, Q111, Q140, Q126, Q2101, Q4812, 1494, Bull and Waters as described above. The 5' untranslated region (5'UTR) was PCR amplified using primers described below, and the amplified fragments were cloned and sequenced as described in Example 5. Two exemplary 5'UTR sequences are presented herein. The 5'UTR sequence of BVDV-I isolate Singer is given as SEQ ID NO:8, and the 5'UTR sequence of BVDV-II isolate Waters is given as SEQ ID NO:9.

Primers BV7 (SEQ ID NO:6) and BV8 (SEQ ID NO:7), were synthesized for the first-strand cDNA and PCR reactions using a Gene Assembler Plus (Pharmacia, Piscataway, N.J.) as above. These sequences were chosen from conserved regions in the genome of five pestiviruses: Osloss (Renard, et al., 1987), NADL (Collett, et al., 1988a), SD-1 (Deng and Brock, 1992), Alfort (Meyers, et al., 1989), and Brescia (Moormann, et al., 1990).

The reverse transcriptase (RT) reaction was performed as above, using 1 $\mu$l of BV7 primer (SEQ ID NO:6, 50 pmol/$\mu$l) instead of $BV_{II}$ or PII-350. The PCR reaction was also carried out as above, using 50 pmol of the BV7 primer (SEQ ID NO:6) and 100 pmol of the BV8 primer (SEQ ID NO:7) instead of the $BV_{II}$/PII-251 or PII-350/PII-251 primer pairs. PCR reaction products were cloned and sequences as above.

A comparison of these polynucleotide sequences, along with those of NADL, SD-1 and Osloss, shown in FIG. 6. The data demonstrate the relatively high degree of homology among the 5'UTR sequences of all the pestiviruses, and the even higher degree of homology among isolates belonging to either group I or group II. Note that this analysis also illustrates a sub-grouping among the group I isolates (indicated in FIG. 6 as group Ia and group Ib).

While the invention has been described with reference to specific methods and embodiments, it is appreciated that various modifications and changes may be made without departing from the invention.

We claim:

1. An immunogenic composition for generating an immune response in a cow against an infection caused by bovine viral diarrhea virus group II (BVDV-II), comprising a chimeric gene operatively coding for a BVDV-II gp53 polypeptide antigen, and a pharmacologically acceptable vehicle, wherein said gene is effective to express said polypeptide antigen in said cow.

2. The composition of claim 1, wherein said gp53 polypeptide antigen has the sequence of SEQ ID NO:2.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 1291 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (vi) ORIGINAL SOURCE:
      (C) INDIVIDUAL ISOLATE: BVDV-II isolate 1494 sequence
          containing gp53 coding region (ix) FEATURE:
      (A) NAME/KEY: CDS
      (B) LOCATION: 1..1269

-continued (xi) SEQUENCE DESCRIPTION: SEQ ID NO:1:

| | | | | | | | | | | | | | | | | |
|---|---|---|---|---|---|---|---|---|---|---|---|---|---|---|---|---|
| TTA | ACT | AGG | ATT | TGG | AAC | GCT | GCC | ACC | ACA | ACA | GCC | TTC | CTA | GTC | TTC | 48 |
| Leu | Thr | Arg | Ile | Trp | Asn | Ala | Ala | Thr | Thr | Thr | Ala | Phe | Leu | Val | Phe | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| CTT | GTG | AAA | GTA | CTG | AGG | GGA | CAA | TTA | ATC | CAA | GGG | CTA | TTG | TGG | CTG | 96 |
| Leu | Val | Lys | Val | Leu | Arg | Gly | Gln | Leu | Ile | Gln | Gly | Leu | Leu | Trp | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| ATG | CTA | ATA | ACA | GGG | GCA | CAG | GGC | TTC | CCT | GAA | TGC | AAA | GAG | GGC | TTC | 144 |
| Met | Leu | Ile | Thr | Gly | Ala | Gln | Gly | Phe | Pro | Glu | Cys | Lys | Glu | Gly | Phe | |
| | | | 35 | | | | | 40 | | | | | 45 | | | |

| | | | | | | | | | | | | | | | | |
|---|---|---|---|---|---|---|---|---|---|---|---|---|---|---|---|---|
| CAA | TAT | GCC | ATA | TCA | AAA | GAC | AAA | AAA | ATA | GGA | CCA | CTG | GGG | CCA | GAG | 192 |
| Gln | Tyr | Ala | Ile | Ser | Lys | Asp | Lys | Lys | Ile | Gly | Pro | Leu | Gly | Pro | Glu | |
| | | 50 | | | | | 55 | | | | | 60 | | | | |

| | | | | | | | | | | | | | | | | |
|---|---|---|---|---|---|---|---|---|---|---|---|---|---|---|---|---|
| AGT | CTA | ACT | ACA | ACA | TGG | CAC | CTT | CCT | ACC | AAA | AAA | ATA | GTG | GAC | TCT | 240 |
| Ser | Leu | Thr | Thr | Thr | Trp | His | Leu | Pro | Thr | Lys | Lys | Ile | Val | Asp | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ATG | GTA | CAG | GTG | TGG | TGT | GAT | GGA | AAA | GAC | TTG | AAA | ATA | TTA | AAA | ACG | 288 |
| Met | Val | Gln | Val | Trp | Cys | Asp | Gly | Lys | Asp | Leu | Lys | Ile | Leu | Lys | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| TGC | ACA | AAG | GAA | GAG | AGG | TAC | TTA | GTG | GCC | GTG | CAC | GAA | AGA | GCC | CTG | 336 |
| Cys | Thr | Lys | Glu | Glu | Arg | Tyr | Leu | Val | Ala | Val | His | Glu | Arg | Ala | Leu | |
| | | | | 100 | | | | | 105 | | | | | 110 | | |

| | | | | | | | | | | | | | | | | |
|---|---|---|---|---|---|---|---|---|---|---|---|---|---|---|---|---|
| TCG | ACC | AGT | GCT | GAG | TTC | ATG | CAG | ATC | AGT | AGT | GGG | ACA | AAA | GGC | CCA | 384 |
| Ser | Thr | Ser | Ala | Glu | Phe | Met | Gln | Ile | Ser | Ser | Gly | Thr | Lys | Gly | Pro | |
| | | | 115 | | | | | 120 | | | | | 125 | | | |

| | | | | | | | | | | | | | | | | |
|---|---|---|---|---|---|---|---|---|---|---|---|---|---|---|---|---|
| GAA | GTG | ATA | GAT | ATG | CCT | GAT | GAC | TTT | GAA | TTT | GGA | CTC | TGC | CCT | TGT | 432 |
| Glu | Val | Ile | Asp | Met | Pro | Asp | Asp | Phe | Glu | Phe | Gly | Leu | Cys | Pro | Cys | |
| | | 130 | | | | | 135 | | | | | 140 | | | | |

| | | | | | | | | | | | | | | | | |
|---|---|---|---|---|---|---|---|---|---|---|---|---|---|---|---|---|
| GAT | TCA | AAA | CCG | GTA | ATA | AAG | GGG | AAG | TTC | AAT | GCC | AGC | TTA | TTG | AAC | 480 |
| Asp | Ser | Lys | Pro | Val | Ile | Lys | Gly | Lys | Phe | Asn | Ala | Ser | Leu | Leu | Asn | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| GGA | CCA | GCT | TTC | CAG | ATG | GTA | TGC | CCA | CAG | GGG | TGG | ACT | GGT | ACA | ATA | 528 |
| Gly | Pro | Ala | Phe | Gln | Met | Val | Cys | Pro | Gln | Gly | Trp | Thr | Gly | Thr | Ile | |
| | | | | 165 | | | | | 170 | | | | | 175 | | |

| | | | | | | | | | | | | | | | | |
|---|---|---|---|---|---|---|---|---|---|---|---|---|---|---|---|---|
| GAA | TAC | ATC | CTG | GCG | AAC | CAA | GAC | ACC | TTG | GAC | ACA | ACT | GTC | GTT | AGG | 576 |
| Glu | Tyr | Ile | Leu | Ala | Asn | Gln | Asp | Thr | Leu | Asp | Thr | Thr | Val | Val | Arg | |
| | | | 180 | | | | | 185 | | | | | 190 | | | |

| | | | | | | | | | | | | | | | | |
|---|---|---|---|---|---|---|---|---|---|---|---|---|---|---|---|---|
| ACA | TAT | AGA | AGA | ACT | ACT | CCA | TTT | CAG | CGG | AGA | AAA | TGG | TGT | ACC | TAT | 624 |
| Thr | Tyr | Arg | Arg | Thr | Thr | Pro | Phe | Gln | Arg | Arg | Lys | Trp | Cys | Thr | Tyr | |
| | | | 195 | | | | | 200 | | | | | 205 | | | |

| | | | | | | | | | | | | | | | | |
|---|---|---|---|---|---|---|---|---|---|---|---|---|---|---|---|---|
| GAA | AAG | ATA | ATA | GGG | GAA | GAT | ATC | CAT | GAA | TGC | ATT | CTA | GGA | GGA | AAC | 672 |
| Glu | Lys | Ile | Ile | Gly | Glu | Asp | Ile | His | Glu | Cys | Ile | Leu | Gly | Gly | Asn | |
| | | 210 | | | | | 215 | | | | | 220 | | | | |

| | | | | | | | | | | | | | | | | |
|---|---|---|---|---|---|---|---|---|---|---|---|---|---|---|---|---|
| TGG | ACA | TGC | ATA | ACT | GGT | GAC | CAT | AGC | AAG | TTG | AAA | GAT | GGG | CCT | ATC | 720 |
| Trp | Thr | Cys | Ile | Thr | Gly | Asp | His | Ser | Lys | Leu | Lys | Asp | Gly | Pro | Ile | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| AAG | AAG | TGT | AAG | TGG | TGT | GGC | TAC | GAC | TTC | TTC | AAT | CCA | GAA | GGA | CTG | 768 |
| Lys | Lys | Cys | Lys | Trp | Cys | Gly | Tyr | Asp | Phe | Phe | Asn | Pro | Glu | Gly | Leu | |
| | | | | 245 | | | | | 250 | | | | | 255 | | |

| | | | | | | | | | | | | | | | | |
|---|---|---|---|---|---|---|---|---|---|---|---|---|---|---|---|---|
| CCA | CAC | TAC | CCA | ATA | GGT | AAG | TGC | ATG | CTC | AGC | AAT | GAG | AGT | GGG | TAC | 816 |
| Pro | His | Tyr | Pro | Ile | Gly | Lys | Cys | Met | Leu | Ser | Asn | Glu | Ser | Gly | Tyr | |
| | | | 260 | | | | | 265 | | | | | 270 | | | |

| | | | | | | | | | | | | | | | | |
|---|---|---|---|---|---|---|---|---|---|---|---|---|---|---|---|---|
| AGG | TTA | GAT | GAC | ACC | TCT | TGT | GAT | AGG | GGT | GGT | GTA | GCC | ATA | GTT | CCA | 864 |
| Arg | Leu | Asp | Asp | Thr | Ser | Cys | Asp | Arg | Gly | Gly | Val | Ala | Ile | Val | Pro | |
| | | | 275 | | | | | 280 | | | | | 285 | | | |

| | | | | | | | | | | | | | | | | |
|---|---|---|---|---|---|---|---|---|---|---|---|---|---|---|---|---|
| ACA | GGT | ACC | GTA | AAG | TGT | AGA | ATA | GGC | AAC | ACC | ACG | GTG | CAG | GTT | ATC | 912 |
| Thr | Gly | Thr | Val | Lys | Cys | Arg | Ile | Gly | Asn | Thr | Thr | Val | Gln | Val | Ile | |
| | | | 290 | | | | | 295 | | | | | 300 | | | |

| | | | | | | | | | | | | | | | | |
|---|---|---|---|---|---|---|---|---|---|---|---|---|---|---|---|---|
| GCT | ACT | AAC | ACT | GAC | CTG | GGA | CCC | ATG | CCC | TGC | AGC | CCA | GCT | GAG | GTG | 960 |
| Ala | Thr | Asn | Thr | Asp | Leu | Gly | Pro | Met | Pro | Cys | Ser | Pro | Ala | Glu | Val | |

|  |  |  |  |  |  |  |  |  |  |  |  |  |  |  |  |
|---|---|---|---|---|---|---|---|---|---|---|---|---|---|---|---|
| ATA | GCA | AGT | GAA | GGA | CCA | GTG | GAA | AAG | ACG | GCA | TGC | ACG | TTT | AAC | TAT | 1008 |
| Ile | Ala | Ser | Glu | Gly | Pro | Val | Glu | Lys | Thr | Ala | Cys | Thr | Phe | Asn | Tyr |
|  |  |  |  | 325 |  |  |  | 330 |  |  |  | 335 |  |  |  |

305 310 315 320

```
ATA GCA AGT GAA GGA CCA GTG GAA AAG ACG GCA TGC ACG TTT AAC TAT        1008
Ile Ala Ser Glu Gly Pro Val Glu Lys Thr Ala Cys Thr Phe Asn Tyr
                325                 330                 335

TCA GAG ACA CTA CCT AAT AAG TAT TAT GAG CCA AGG GAC CGG TAC TTC        1056
Ser Glu Thr Leu Pro Asn Lys Tyr Tyr Glu Pro Arg Asp Arg Tyr Phe
                340                 345                 350

CAA CAA TAC ATG TTA AAA GGG AAG TGG CAA TAT TGG TTT GAC CTG GAT        1104
Gln Gln Tyr Met Leu Lys Gly Lys Trp Gln Tyr Trp Phe Asp Leu Asp
                355                 360                 365

TCT ATA GAC CAC CAC AAA GAC TAC TTT TCA GAG TTC ATA GTT ATA GCA        1152
Ser Ile Asp His His Lys Asp Tyr Phe Ser Glu Phe Ile Val Ile Ala
            370                 375                 380

GTG GTA GCC TTG CTA GGT GGT AAG TAT GTA CTG TGG CTC TTA GTA ACA        1200
Val Val Ala Leu Leu Gly Gly Lys Tyr Val Leu Trp Leu Leu Val Thr
385                 390                 395                 400

TAT ATG ATA CTG TCT GAG CAG ATG GCT ATG GGT GCT GGA GTA AGT ACC        1248
Tyr Met Ile Leu Ser Glu Gln Met ala Met Gly Ala Gly Val Ser Thr
                405                 410                 415

GAA GAG ATA GTC ATG ATG GTC TAA CTG CTT ATG TAG TAT CTT C              1291
Glu Glu Ile Val Met Met Val
                420
```

(2) INFORMATION FOR SEQ ID NO:2:

(i) SEQUENCE CHARACTERISTICS:
        (A) LENGTH: 423 amino acids
        (B) TYPE: amino acid
        (D) TOPOLOGY: linear (ii) MOLECULE TYPE: protein (xi) SEQUENCE DESCRIPTION: SEQ ID NO:2:

```
Leu Thr Arg Ile Trp Asn Ala Ala Thr Thr Thr Ala Phe Leu Val Phe
 1               5                  10                  15

Leu Val Lys Val Leu Arg Gly Gln Leu Ile Gln Gly Leu Leu Trp Leu
                20                  25                  30

Met Leu Ile Thr Gly Ala Gln Gly Phe Pro Glu Cys Lys Glu Gly Phe
            35                  40                  45

Gln Tyr Ala Ile Ser Lys Asp Lys Lys Ile Gly Pro Leu Gly Pro Glu
    50                  55                  60

Ser Leu Thr Thr Thr Trp His Leu Pro Thr Lys Lys Ile Val Asp Ser
65                  70                  75                  80

Met Val Gln Val Trp Cys Asp Gly Lys Asp Leu Lys Ile Leu Lys Thr
                85                  90                  95

Cys Thr Lys Glu Glu Arg Tyr Leu Val Ala Val His Glu Arg Ala Leu
                100                 105                 110

Ser Thr Ser Ala Glu Phe Met Gln Ile Ser Ser Gly Thr Lys Gly Pro
            115                 120                 125

Glu Val Ile Asp Met Pro Asp Asp Phe Glu Phe Gly Leu Cys Pro Cys
    130                 135                 140

Asp Ser Lys Pro Val Ile Lys Gly Lys Phe Asn Ala Ser Leu Leu Asn
145                 150                 155                 160

Gly Pro Ala Phe Gln Met Val Cys Pro Gln Gly Trp Thr Gly Thr Ile
                165                 170                 175

Glu Tyr Ile Leu Ala Asn Gln Asp Thr Leu Asp Thr Thr Val Val Arg
            180                 185                 190

Thr Tyr Arg Arg Thr Thr Pro Phe Gln Arg Arg Lys Trp Cys Thr Tyr
    195                 200                 205
```

```
Glu Lys Ile Ile Gly Glu Asp Ile His Glu Cys Ile Leu Gly Gly Asn
210                 215                 220

Trp Thr Cys Ile Thr Gly Asp His Ser Lys Leu Lys Asp Gly Pro Ile
225                 230                 235                 240

Lys Lys Cys Lys Trp Cys Gly Tyr Asp Phe Phe Asn Pro Glu Gly Leu
                245                 250                 255

Pro His Tyr Pro Ile Gly Lys Cys Met Leu Ser Asn Glu Ser Gly Tyr
                260                 265                 270

Arg Leu Asp Asp Thr Ser Cys Asp Arg Gly Val Ala Ile Val Pro
                275                 280                 285

Thr Gly Thr Val Lys Cys Arg Ile Gly Asn Thr Thr Val Gln Val Ile
290                 295                 300

Ala Thr Asn Thr Asp Leu Gly Pro Met Pro Cys Ser Pro Ala Glu Val
305                 310                 315                 320

Ile Ala Ser Glu Gly Pro Val Glu Lys Thr Ala Cys Thr Phe Asn Tyr
                325                 330                 335

Ser Glu Thr Leu Pro Asn Lys Tyr Tyr Glu Pro Arg Asp Arg Tyr Phe
                340                 345                 350

Gln Gln Tyr Met Leu Lys Gly Lys Trp Gln Tyr Trp Phe Asp Leu Asp
                355                 360                 365

Ser Ile Asp His His Lys Asp Tyr Phe Ser Glu Phe Ile Val Ile Ala
                370                 375                 380

Val Val Ala Leu Leu Gly Gly Lys Tyr Val Leu Trp Leu Leu Val Thr
385                 390                 395                 400

Tyr Met Ile Leu Ser Glu Gln Met ala Met Gly Ala Gly Val Ser Thr
                405                 410                 415

Glu Glu Ile Val Met Met Val
                420

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer BVII (3630 vicinity)

(xi) SEQUENCE DESCRIPTION: SEQ ID NO:3:

CAGAGATCTC ATAGCAAGTT GCCCATCAT                                           29

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO
```

(vi) ORIGINAL SOURCE:
          (C) INDIVIDUAL ISOLATE: Primer pII-350 (3500 vicinity)

(xi) SEQUENCE DESCRIPTION: SEQ ID NO:4:

CAGAGTTCAT AGTTATAGCR GT                                          22

(2) INFORMATION FOR SEQ ID NO:5:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (iii) HYPOTHETICAL: NO (iv) ANTI-SENSE: NO (vi) ORIGINAL SOURCE:
          (C) INDIVIDUAL ISOLATE: Primer pII-251 (2400 vicinity)

(xi) SEQUENCE DESCRIPTION: SEQ ID NO:5:

TAACWNGSAT WTGGAACSCT GC                                          22

(2) INFORMATION FOR SEQ ID NO:6:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (iii) HYPOTHETICAL: NO (iv) ANTI-SENSE: NO (vi) ORIGINAL SOURCE:
          (C) INDIVIDUAL ISOLATE: Primer BV7 (NADL
               nucleotides 392-372)

(xi) SEQUENCE DESCRIPTION: SEQ ID NO:6:

ACTCCATGTG CCATGTACAG C                                           21

(2) INFORMATION FOR SEQ ID NO:7:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (iii) HYPOTHETICAL: NO (iv) ANTI-SENSE: NO (vi) ORIGINAL SOURCE:
          (C) INDIVIDUAL ISOLATE: Primer BV8 (NADL
               nucleotides 103-123)

(xi) SEQUENCE DESCRIPTION: SEQ ID NO:7:

TAGCCATGCC CTTAGTAGGA C                                           21

(2) INFORMATION FOR SEQ ID NO:8:

(i) SEQUENCE CHARACTERISTICS:
          (A) LENGTH: 248 base pairs

```
            (B) TYPE: nucleic acid
            (C) STRANDEDNESS: unknown
            (D) TOPOLOGY: unknown (ii) MOLECULE TYPE: cDNA to mRNA (iii) HYPOTHETICAL: NO (iv) ANTI-SENSE: NO (vi) ORIGINAL SOURCE:
            (C) INDIVIDUAL ISOLATE: BVDV Strain Singer 5' untranslated
                region (bases 1-248)

(xi) SEQUENCE DESCRIPTION: SEQ ID NO:8:

TAGCATAAAG AGGGGGGTAG CAGCAGTGGT GAGTTCGTTG GATGGCTTAA GCCCTGAGTA      60

CAGGGTAGTC GTCAGTGGTT CGACGCCTTG GAATAAAGGT CTCGAGATGC CACGTGGACG     120

AGGGCATGCC CAAAGCACAT CTTAACCTGA GCGGGGGTCG CCCAGGTAAA AGCAGTTCTA     180

ACCGACTGTT ACGGATACAG CCTGATAGGG TGCTGCAGAG GCCCACTGTT CTGCTACTAA     240

AAATCTCT                                                              248

(2) INFORMATION FOR SEQ ID NO:9:

(i) SEQUENCE CHARACTERISTICS:
            (A) LENGTH: 248 base pairs
            (B) TYPE: nucleic acid
            (C) STRANDEDNESS: unknown
            (D) TOPOLOGY: unknown (ii) MOLECULE TYPE: cDNA to mRNA (iii) HYPOTHETICAL: NO (iv) ANTI-SENSE: NO (vi) ORIGINAL SOURCE:
            (C) INDIVIDUAL ISOLATE: BVDV Strain Waters 5' untranslated
                region (bases 1-248)

(xi) SEQUENCE DESCRIPTION: SEQ ID NO:9:

TAGCAAAAGG AGGGGACTAG CGGTAGCAGT GAGTTCGTTG GATGGCCGAA CCCCTGAGTA      60

CAGGGGAGTC GTCAATGGTT CGACACTCCA TTAGTCGAGG AGTCTCGAGA TGCCATGTGG     120

ACGAGGGCAT GCCCACGGCA CATCTTAACC CATGCGGGGG TTGCATGGGT GAAAGCGCTA     180

TTCGTGGCGT TATGGACACA GCCTGATAGG GTGTAGCAGA GACCTGCTAT TCCGCTAGTA     240

AAAACTCT                                                              248

(2) INFORMATION FOR SEQ ID NO:10:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
            (C) INDIVIDUAL ISOLATE: Primer 1A (xi) SEQUENCE DESCRIPTION: SEQ ID NO:10:

GGAAGATCTA TGTTTTTAGT ATGCCTTGT                                        29
```

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer 1B (xi) SEQUENCE DESCRIPTION: SEQ ID NO:11:

CGAAGATCTC ACTTCTGTTC TGATAAGA        28

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer 2A (xi) SEQUENCE DESCRIPTION: SEQ ID NO:12:

AGATCCATGG TTTTAGTATG CCTTGT        26

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer 2B (xi) SEQUENCE DESCRIPTION: SEQ ID NO:13:

CGAGTCGACC TATATGGCTC AGCGAAG        27